United States Patent [19]
Erion et al.

[11] Patent Number: 5,506,347
[45] Date of Patent: Apr. 9, 1996

[54] LYXOFURANOSYL ANALOGUES OF ADENOSINE

[75] Inventors: Mark D. Erion, Del Mar; Bheemarao G. Ugarkar, Escondido; Angelo J. Castellino, San Diego, all of Calif.

[73] Assignee: Gensia, Inc., San Diego, Calif.

[21] Appl. No.: 191,282

[22] Filed: Feb. 3, 1994

Related U.S. Application Data

[63] Continuation-in-part of Ser. No. 182,381, Jan. 13, 1994, abandoned, which is a continuation-in-part of Ser. No. 14,159, Feb. 3, 1993, abandoned.

[51] Int. Cl.[6] .............................. C07G 3/00; C07H 19/16
[52] U.S. Cl. ..................... 536/4.1; 536/27.2; 536/27.4; 536/27.62; 536/27.13; 544/264; 544/254; 544/262; 544/280; 544/265; 544/266; 544/267; 544/271; 544/272; 544/273; 544/277
[58] Field of Search ................................. 536/27.2, 27.4, 536/27.62, 4.1; 514/45, 46; 544/264, 254, 262, 280, 265, 266, 267, 271, 272, 273, 277

[56] References Cited

FOREIGN PATENT DOCUMENTS 0496617  7/1992  European Pat. Off. ............. 536/27.2

OTHER PUBLICATIONS

Gupta et al., "Relationship Between Structure and Antiviral Activity of 5–Methoxymethyl-2'–Deoxyuridine and 5–Methoxymethyl-1–(2'deoxy-α-D-lyxofuranosyl)uracil," *Antiviral Research*, 7, 69–77 (1987).

Ealick et al., "Application of Crystallographic and Modeling Methods in the Design of Purine Nucleoside Phosphorylase Inhibitors," *Proc. Nat. Acad. Sci. USA*, 88, 11540–11544 (1991).

Bennett et al., "Structural Requirments for Activity of Nucleosides as Substrates for Adenosine Kinase. Orientation of Substituents on the Pentofuranosyl Ring," *Mol. Pharmacol.*, 11(6), 803–808 (1975); *Chem. Abstr.*, 84, p. 173, Abstract No. 40185e (1976); only Abstract supplied.

K. H. Scheit, "Nucletides with Altered Sugar Parts. Arabino, Xylo and Lyxo Nucleotide Analogs," Ch. 5.1 in *Nucleotide Analogs, Synthesis and Biological Function*, Wiley–Interscience, New York, 1980, pp. 151–153 and 190–191.

*Primary Examiner*—Douglas W. Robinson
*Assistant Examiner*—L. Eric Crane
*Attorney, Agent, or Firm*—Lyon & Lyon

[57] ABSTRACT

Novel lyxose derivatives which selectively inhibit adenosine kinase and methods of preparing these compounds are provided. These compounds are useful in treating certain conditions in vivo which may be ameliorated by increased local concentrations of adenosine.

51 Claims, 3 Drawing Sheets

स5,506,347

LYXOFURANOSYL ANALOGUES OF ADENOSINE

RELATED APPLICATIONS

This application is a continuation-in-part of application Ser. No. 08/192,391, filed Jan. 13, 1994, now abandoned, which is a continuation-in-part of application Ser. No. 09/014,159, filed Feb. 3, 1993, now abandoned.

FIELD OF INVENTION

This invention relates to adenosine kinase inhibitors and to novel nucleoside lyxofuranosyl analogs, specifically to purine, pyrrolo[2,3-d]pyrimidine and pyrazolo[3,4-d]pyrimidine nucleoside analogs having activity as adenosine kinase inhibitors. The invention also relates to the preparation and use of these and other adenosine kinase inhibitors in the treatment of cardiovascular, and cerebrovascular diseases, central nervous system disorders, seizures, pain, inflammation, sepsis, septic shock, endotoxemia and other diseases.

BACKGROUND OF THE INVENTION

Adenosine has been reported to have cardioprotective and neuroprotective properties. It is reportedly released from cells in response to alterations in the supply of or demand for oxygen, is said to be a potent vasodilator, and is believed to be involved in the metabolic regulation of blood flow. However, adenosine has a short half life (<1 sec) in human blood, and therefore high doses of adenosine would need to be administered continuously to achieve effective levels. Adenosine has been reported to exhibit negative inotropic, chronotropic and dromotropic effects and to cause coronary steal by preferentially dilating vessels in nonischemic regions. Consequently, high doses of adenosine are toxic and severely limit its therapeutic potential. However, it is believed that by increasing adenosine concentration locally, i.e. at the target site within the target tissue, the beneficial effects of adenosine can be provided and the toxic systemic effects minimized.

Adenosine kinase is a cytosolic enzyme which catalyzes the phosphorylation of adenosine to AMP. Inhibition of adenosine kinase can potentially reduce the ability of the cell to utilize adenosine, leading to increased adenosine outside of the cell where it is pharmacologically active. However, the regulation of adenosine concentration is complex and involves other adenosine-metabolizing enzymes each with different kinetic properties and mechanisms of regulation.

A number of nucleosides including purine, pyrrolo[2,3-d]pyrimidine and pyrazolo[3,4-d]pyrimidine analogs have been evaluated for inhibition of adenosine kinase but were reported to have $K_i$'s of greater than 800 nM (Caldwell and Henderson *Cancer Chemother. Rep.*, 1971 2: 237–246; Miller et al., *J. Biol. Chem.*, 1979, 254: 2346–2352). A few compounds have been reported as potent inhibitors of adenosine kinase with $K_i$'s of less than 100 nM. These are the purine nucleosides, 5'-amino-5'-deoxyadenosine (Miller et al., *J. Biol. Chem.*, 1979, 254: 2346–2352) and 1,12-bis(adenosin-$N^6$-yl)dodecane (Prescott et al., *Nucleosides & Nucleotides*, 1989, 8: 297), and the pyrrolopyrimidine nucleosides, 5-iodotubercidin (Henderson et al., *Cancer Chemotherapy Rep. Part 2*, 1972, 3: 71–85; Bontemps et al., *Proc. Natl. Acad. Sci. USA*, 1983, 80: 2829–2833; Davies et al., *Biochem. Pharmacol.*, 1986, 35: 3021–3029) and 5'-deoxy-5-iodotubercidin (Davies et al., *Biochem. Pharmacol.*, 1984, 33: 347–355; Davies et al., *Biochem. Pharmacol.*, 1986, 35: 3021–3029).

Some of these compounds have been used to evaluate whether adenosine kinase inhibition might lead to increased extracellular adenosine concentrations. In rat cardiomyocytes, inhibition of adenosine deaminase by 2'-deoxycoformycin was reported to have no effect on adenosine release from the cells. In contrast, inhibition of ADA together with adenosine kinase by 5'-amino-5'-deoxyadenosine resulted in a 6-fold increase in adenosine release (Zoref-Shani et al., *J. Mol. Cell. Cardiol.*, 1988, 20: 23–33). The effects of the adenosine kinase inhibitor alone were not reported.

Although the adenosine kinase inhibitors, 5'-amino-5'-deoxyadenosine and 5-iodotubercidin have been widely used in experimental models, the susceptibility of 5'-amino-5'-deoxyadenosine to deamination, and hence its potentially short half life, and the cytotoxicity of 5-iodotubercidin make their clinical utility limited and may limit interpretations based on these compounds. The pyrrolo[2,3-d]pyrimidines, 5-iodotubercidin and 5'-deoxy-5-iodotubercidin have been reported to cause pronounced general flaccidity and much reduced spontaneous locomotor activity in mice, interpreted to be skeletal muscle relaxation; to cause hypothermia in mice; and to decrease blood pressure and heart rate in anesthetized rats (Daves et al., *Biochem. Pharmacol.*, 1984, 33: 347–355; Daves et al., *Biochem. Pharmacol.*, 1986, 35: 3021–3029; U.S. Pat. No. 4,455,420). The skeletal muscle effects of these compounds have been poorly documented, while the other effects were considered significant toxicities.

Lyxofuranosyl adenine compounds have been reported. (Miller, R. L. et al., *J. Biol. Chem.*, 1979, 254; 2346–2352; Agarwal, K. C. et al., *Biochem. Pharmacol.*, 1979, 28, 501–510; Bennett, Jr., L. L. et al., *Mol. Pharmacol.*, 1975, 11, 803–808). In particular, 9-α-L-lyxofuranosyl adenine has been reported to be a substrate for adenosine kinase, albeit with a much decreased efficiency relative to adenosine.

The commonly assigned U.S. Ser. No. 07/812,916, "Adenosine Kinase Inhibitors", filed Dec. 23, 1991 describes certain purine, pyrrolo[2,3-d] pyrimidine and pyrazolo[3,4-d]pyrimidine ribofuranosyl analogs which have activity as adenosine kinase inhibitors.

SUMMARY OF THE INVENTION

The present invention is directed to novel compounds which are lyxofuranosyl derivatives and which are potent and selective inhibitors of adenosine kinase.

In one aspect, the present invention is directed to certain novel compounds which inhibit adenosine kinase, to the preparation of these compounds, and to the in vitro and in vivo adenosine kinase inhibition activity of these compounds. Another aspect of the present invention is directed to the clinical use of adenosine kinase inhibitors as a method of increasing adenosine concentrations in biological systems. In vivo inhibition of adenosine kinase prevents phosphorylation of adenosine which results in higher local concentrations of endogenous adenosine. As a result of the very short half-life of adenosine and very low quantities of adenosine in tissues, the effect caused by inhibition of adenosine kinase is most pronounced in regions producing the most adenosine such as ischemic regions (where there is net ATP catabolism in relation to ATP synthesis). In this way the beneficial effects of adenosine are enhanced in a site and event specific manner and toxic systemic effects are reduced.

Among other factors, the present invention is based on our finding that the novel compounds of the present invention are useful as adenosine kinase inhibitors and act to elevate and prolong extracellular adenosine levels and thereby enhance the pharmacological benefits of adenosine. These compounds are especially useful for the treatment of conditions and disorders responsive to the inhibition of adenosine kinase, particularly cardiovascular disorders, including cardiac arrhythmias and especially conditions related to ischemia such as myocardial infarction, angina, percutaneous transluminal coronary angiography (PTCA), and other thrombotic and embolic disorders.

The compounds are also useful in treating disorders such as stroke, neurologic disorders such as seizure or psychosis, and other conditions benefitted by enhanced adenosine levels (at a selected locus) including inflammation, arthritis, autoimmune disease, ulcers and irritable bowel syndrome. Further, the compounds of the present invention are especially useful in the treatment of septic shock, sepsis and endotoxemia. In addition, these compounds are useful as muscle relaxants and in inducing sleep and in treating anxiety.

The present invention is further directed to the prophylactic and affirmative treatment of pain. For example, adenosine kinase inhibitors will be useful in the treatment of acute and chronic pain.

The present invention is further directed to methods of treatment of inflammatory disorders, and in particular to the treatment of inflammatory disorders such as arthritis, and especially rheumatoid arthritis. Current treatments such as administration of non-steroidal anti-inflammatory agents, although they decrease inflammation, they do not decrease joint destruction. Therefore, the methods of the present invention represent an advance over current methods of therapy (see example E).

Accordingly, the present invention is directed to novel compounds that may be used clinically to treat medical conditions where an increased local adenosine concentration is beneficial. These compounds comprise novel pyrrolopyrimidine and pyrazolopyrimidine and purine derivatives that are substituted with a lyxofuranosyl derivative as specified below in formula A.

Since these compounds may have asymmetric centers other than those of the lyxofuranosyl ring, the present invention is directed not only to racemic mixtures of these compounds, but to individual stereoisomers. The present invention also includes pharmaceutically acceptable and/or useful salts of the compounds of formula A, including acid addition salts. These salts may be formed by the addition of hydrobromic, hydrochloric, sulfuric and like acids or by the addition of carboxylic or sulfonic and like acids. Also included in the scope of the present invention are prodrugs of the compounds of formula A.

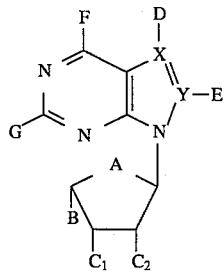

Formula A

DEFINITIONS

In accordance with the present invention and as used herein, the following terms are defined with the following meanings, unless explicitly stated otherwise.

The term "aryl" refers to aromatic groups which have at least one ring having a conjugated pi electron system and includes carbocyclic aryl, heterocyclic aryl and biaryl groups, all of which may be optionally substituted.

Heterocyclic aryl groups are groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

Carbocyclic aryl groups are groups wherein the ring atoms on the aromatic ring are carbon atoms. Carbocyclic aryl groups include monocyclic carbocyclic aryl groups and optionally substituted naphthyl groups.

The term "optionally substituted" includes groups substituted by one to four substituents, being independently selected from lower alkyl, hydroxy, lower alkoxy, lower alkanoyloxy, halogen, carboxy, carboxyalkyl, cyano, nitro, trihalomethyl, amino, lower alkylamino, lower acylamino or lower alkoxycarbonyl.

The term "aralkyl" refers to an alkyl group substituted with an aryl group. Suitable aralkyl groups include benzyl, picolyl, and the like, and may be optionally substituted.

The term "lower" referred to herein in connection with organic radicals or compounds respectively defines such as with up to and including 10, preferably up to and including 6 and advantageously one or two carbon atoms. Such groups may be straight chain or branched.

The terms (a) "alkylamino", (b) "arylamino", and (c) "aralkylamino", respectively, refer to the groups —NRR' wherein respectively, (a) R is alkyl and R' is hydrogen or alkyl; (b) R is aryl and R' is hydrogen or aryl, and (c) R is aralkyl and R' is hydrogen or aralkyl.

The term "carboxamide" or "carboxamido" refers to —CONR$_2$ where each R is independently hydrogen or alkyl.

The term "alkyl" refers to saturated aliphatic groups including straight-chain, branched chain and cyclic groups.

The term "alkenyl" refers to unsaturated groups which contain at least one carbon-carbon double bond and includes straight-chain, branched-chain and cyclic groups.

The term "alkynyl" refers to unsaturated groups which contain at least one carbon-carbon triple bond and includes straight-chain, branched-chain and cyclic groups.

The term "alkylene" refers to a divalent straight chain or branched chain saturated aliphatic radical.

The term "lower cyclic ring containing two or more oxygen atoms" refers to cyclic groups used to protect 1,2-diols and which on treatment with the appropriate chemical reagents release the 1,2-diol. These cyclic protecting groups are well known in the art and include but are not limited to ethylene carbonate and 2,2-dimethyl-1,3-dioxolane and orthoesters well known in the art.

The term "aminocarboxyalkyl" refers to the group "—N(R$_1$)—C(O)—O—R$_2$" where R$_1$ is lower alkyl or hydrogen and R$_2$ is alkyl.

The term "prodrug" as used herein refers to any compound that may have less intrinsic activity than the "drug" but when administered to a biological system generates the "drug" substance either as a result of spontaneous chemical reaction or by enzyme catalyzed or metabolic reaction. Reference is made to various prodrugs such as acyl esters, carbonates, and urethanes, included herein. The groups illustrated are exemplary, not exhaustive and one skilled in the art could prepare other known varieties of prodrugs.

Such prodrugs of the compounds of Formula A, fall within the scope of the present invention.

The term "pharmaceutically acceptable salt" includes salts of compounds of Formula A derived from the combination of a compound of this invention and an organic or inorganic acid. The compounds of Formula A are useful in both free base and salt form. In practice the use of salt form amounts to use of base form; both forms are within the scope of the present invention.

The terms "anilino" and "phenylamino" are used interchangeably to represent the group —NH-phenyl.

DETAILED DESCRIPTION OF THE INVENTION

Novel Lyxofuranosyl-Derivative Compounds

Figure 1:
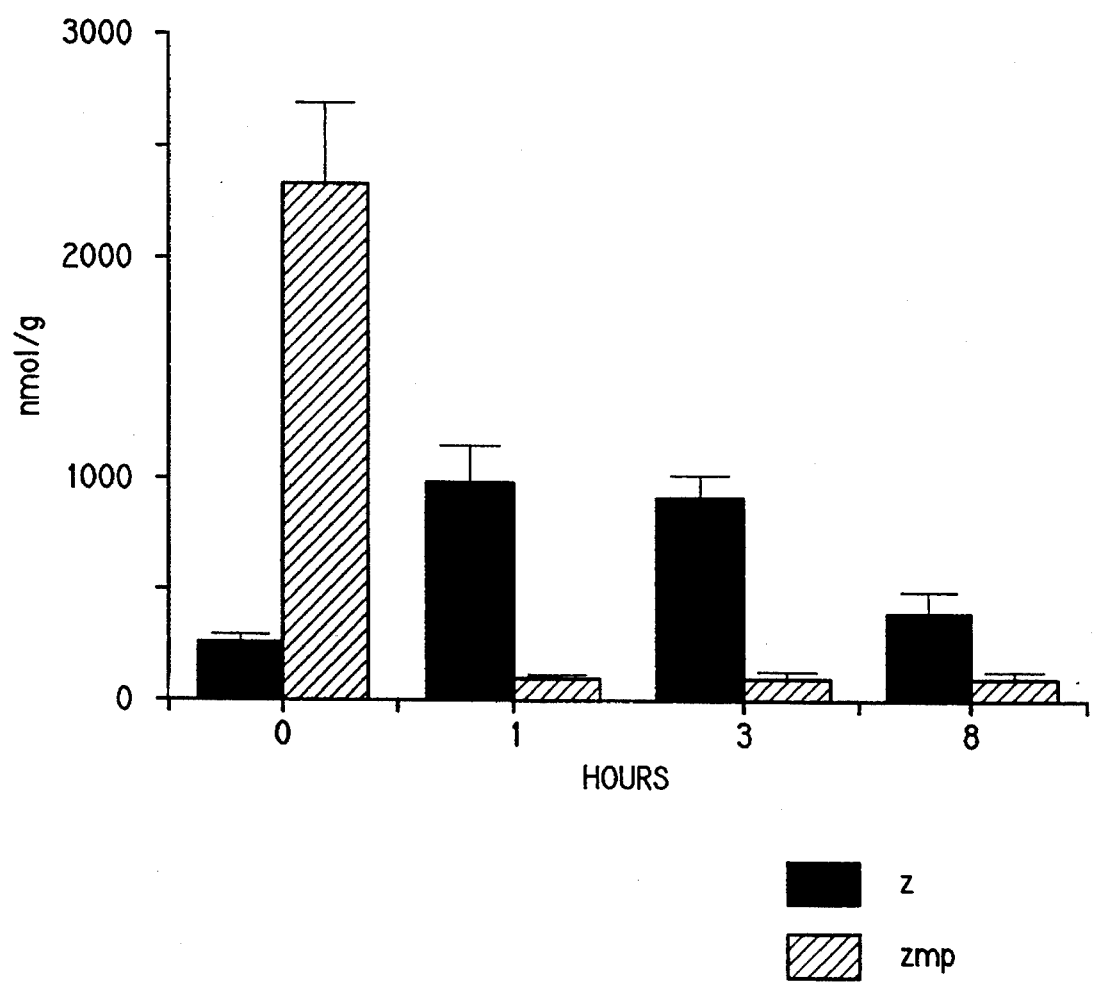
FIG. 1 depicts acadesine and ZMP levels in heart tissue after IV administration of one of the compounds of the present invention as described in Example C.

Preferred compounds of the present invention are adenosine kinase inhibitors comprising lyxose derivatives of the following formula.

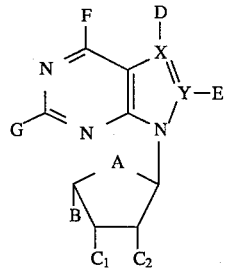

Formula A wherein

A is oxygen, methylene or sulfur;

B is carboxyl, carboxyalkyl, carboxamido, alkenyl, or —$(CH_2)_n$—B' where n is an integer from 1 to 5 and B' is hydrogen, hydroxy, lower alkyl esters or carbonate esters thereof, alkyl, alkoxy, amino, alkylamino, mercapto, alkylthio, halogen, azido, cyano, aminocarboxyalkyl, or amidoalkyl;

$C_1$ and $C_2$ are independently hydrogen, hydroxyl or lower alkyl esters or carbonate esters thereof, or when taken together form a lower cyclic ring containing two or more oxygen atoms;

X and Y are independently carbon or nitrogen, however both X and Y cannot be nitrogen;

D is halogen, alkyl, aryl, aralkyl, alkenyl, alkynyl, alkoxy, cyano, cyanoalkyl, carboxamido, aryloxy, amino, alkylamino, arylamino, aralkylamino, alkylthio, or arylthio, all optionally substituted, when X is carbon, and is null when X is nitrogen;

E is hydrogen, halogen, alkyl, alkylamino, alkylthio or azido when Y is carbon and is null when Y is nitrogen;

F is amino, hydrogen, halogen, alkoxy, alkylthio, aryl, alkyl, alkylamino, arylamino, or aralkylamino, all optionally substituted;

G is hydrogen, lower alkyl, halogen, alkoxy or alkylthio;

and pharmaceutically acceptable salts thereof;

with the proviso that when X is nitrogen and Y is carbon, E and G are hydrogen and F is amino, then B is not methyl, hydroxymethyl or vinyl.

Preferred Compounds

Suitable alkyl groups include groups having from one to about twenty carbon atoms. Suitable alkenyl and alkynyl groups include groups having from two to about twenty carbon atoms. Suitable aryl groups include groups having from one to about twenty carbon atoms. Suitable aralkyl groups include having from two to about twenty-one carbon atoms. Suitable acyloxy groups include groups having from two to about twenty carbon atoms.

In general, preferred are compounds where A is oxygen or carbon. Especially preferred are compounds where A is oxygen.

Preferred include those compounds where B is vinyl or —$(CH_2)_n$—B' where n is 1 and B' is lower alkyl, lower alkoxy or lower alkyl esters and especially preferred where B' is hydrogen, hydroxy or amino.

Preferred are compounds where $C_1$ and C2 are hydrogen and especially preferred are compounds where $C_1$ and $C_2$ are both hydroxy or lower alkyl esters or carbonates thereof, or when taken together form a lower cyclic ring containing two or more oxygens.

Especially preferred are compounds where E and G are hydrogen.

Preferred are compounds where D is halogen or optionally substituted aryl including heteroaryl and especially preferred are compounds where D is iodo, bromo, optionally substituted phenyl, optionally substituted furanyl and optionally substituted thienyl. Preferred substituents are halogen, lower alkyl, lower alkoxy, and carboxyl.

Preferred are compounds where F is alkylamino, optionally substituted arylamino or halogen and especially preferred are compounds where F is amino, anilino or substituted anilino. Preferred substituents are halogen, lower alkyl lower alkoxy, cyano, and carboxyl.

A. In General

The compounds of the present invention contain asymmetric carbon atoms and hence can exist as stereoisomers, both enantiomers and diastereomers. The individual preferred stereoisomers and mixtures thereof are considered to fall within the scope of the present invention. The compounds described by formula A contain a modified 1-α-L-lyxofuranosyl group and that isomer comprises a particularly preferred diastereomeric and enantiomeric form for compounds of the present invention. Aptly, the synthetic examples set forth herein provide the preferred isomer. It is evident that, in addition to the sugar moiety, additional asymmetric carbons may be present in the compounds of Formula A. In such an event, the resulting diastereomers are considered to fall within the scope of the present invention.

Examples of preferred compounds include, but are not limited to:

Preferred are the following compounds:

5-Iodo-4-(phenylamino)-7-(1-alpha-L-lyxofuranosyl)pyrrolo[ 2,3-d]pyrimidine,

4-Chloro-5-Iodo-7-(5-O-methyl-1-alpha-L-lyxofuranosyl)pyrrolo[ 2,3-d]pyrimidine, 4-Amino-5-Iodo-7-(5-O-methyl-1-alpha-L-lyxofuranosyl)pyrrolo[2,3-d]pyrimidine, 5-Phenyl-4-(phenylamino)-7-(5-O-methyl-1-alpha-L-lyxofuranosyl)pyrrolo[2,3-d]pyrimidine, 4-Amino-5-iodo-7-(5-chloro-5-deoxy-1-alpha-L-lyxofuranosyl)pyrrolo[2,3-d]pyrimidine, 4-Amino-5-iodo-7-(5-bromo-5-deoxy-1-alpha-L-lyxofuranosyl)pyrrolo[2,3-d]pyrimidine, 4-Amino-5-iodo-7-(5,6-dideoxy-1-beta-D-gulofuranosyl)pyrrolo[2,3-d]pyrimidine 4-Amino-5-iodo-7-(5,6-didehydro-5,6-dideoxy-1-beta-D-gulofuranosyl)pyrrolo[2,3-d]pyrimidine, 4-Amino-5-bromo-7-(5-O-methyl-1-alpha-L-lyxofuranosyl)pyrrolo[2,3-d]pyrimidine, 4-Amino-5-bromo-7-(5-chloro-5-deoxy-1-alpha-L-lyxofuranosyl)pyrrolo[2,3-d]pyrimidine, 4-Amino-5-bromo-7-(5,6-dideoxy-1-beta-D-gulofuranosyl)pyrrolo[2,3-d]pyrimidine, 4-(Phenylamino)-5-phenyl-7-(5-O-methyl-1-alpha-L-lyxofuranosyl)pyrrolo[2,3-d]pyrimidine, 4-(Phenylamino)-5-phenyl-7-(5-deoxy-1-beta-D-gulofuranosyl)pyrrolo[2,3-d]pyrimidine, 4-(phenylamino)-5-phenyl-7-(5-chloro-5-deoxy-1-alpha-L-lyxofuranosyl)pyrrolo[2,3-d]pyrimidine, 4-(Phenylamino)-5-phenyl-7-(5-deoxy-1-alpha-L-lyxofuranosyl)pyrrolo[2,3-d]pyrimidine, 4-(Phenylamino)-5-phenyl-7-(5,6-dideoxy-1-beta-D-gulofuranosyl)pyrrolo[2,3-d]pyrimidine, 4-(Phenylamino)-5-phenyl-7-(5,6-didehydro-5,6-dideoxy-1-beta-D-gulofuranosyl)pyrrolo[2,3-d]pyrimidine, 4-(Phenylamino)-5-(4-methoxyphenyl)-7-(1-alpha-L-lyxofuranosyl)pyrrolo[2,3-d]pyrimidine, 4-(Phenylamino)-5-(4-chlorophenyl)-7-(1-alpha-L-lyxofuranosyl)pyrrolo[2,3-d]pyrimidine, 4-(Phenylamino)-5-(4-carboxamidophenyl)-7-(1-alpha-L-lyxofuranosyl)pyrrolo[2,3-d]pyrimidine, 4-(Phenylamino)-5-(4-methoxyphenyl)-7-(5-amino-5-deoxy-1-alpha-L-lyxofuranosyl)pyrrolo[2,3-d]pyrimidine, 4-(Phenylamino)-5-(4-chlorophenyl)-7-(5-amino-5-deoxy-1-alpha-L-lyxofuranosyl)pyrrolo[2,3-d]pyrimidine, 4-(Phenylamino)-5-(4-carboxamidophenyl)-7-(5-amino-5-deoxy-1-alpha-L-lyxofuranosyl)pyrrolo[2,3-d]pyrimidine, 4-(Phenylamino)-5-(4-chlorophenyl)-7-(5-deoxy-1-alpha-L-lyxofuranosyl)pyrrolo[2,3-d]pyrimidine, 4-(Phenylamino)-5-(4-carboxamidophenyl)-7-(5-deoxy-1-alpha-L-lyxofuranosyl)pyrrolo[2,3-d]pyrimidine, 4-[(4-Carboxamidophenyl)amino]-5-phenyl-7-(1-alpha-L-lyxofuranosyl)pyrrolo[2,3-d]pyrimidine, 4-[(4-Carboxamidophenyl)amino]-5-phenyl-7-(5-amino-5-deoxy-1-alpha-L-lyxofuranosyl)pyrrolo[2,3-d]pyrimidine, 4-(4-Chlorophenylamino)-5-phenyl-7-(5-deoxy-1-alpha-L-lyxofuranosyl)pyrrolo[2,3-d]pyrimidine, 4-[(4-Carboxamidophenyl)amino]-5-phenyl-7-(5-deoxy-1-alpha-L-lyxofuranosyl)pyrrolo[2,3-d]pyrimidine, 4-(Phenylamino)-5-(2-thienyl)-7-(5-deoxy-1-alpha-L-lyxofuranosyl)pyrrolo[2,3-d]pyrimidine, 4-(Phenylamino)-5-(2-furanyl)-7-(5-deoxy-1-alpha-L-lyxofuranosyl)pyrrolo[2,3-d]pyrimidine, 9-(5-Amino-5-deoxy-1-alpha-L-lyxofuranosyl)adenine, 2-Bromo-9-(5-amino-5-deoxy-1-alpha-L-lyxofuranosyl)adenine, 2-Chloro-9-(5-amino-5-deoxy-1-alpha-L-lyxofuranosyl)adenine, 2-Fluoro-9-(5-amino-5-deoxy-1-alpha-L-lyxofuranosyl)adenine, 2-Methyl-9-(5-amino-5-deoxy-1-alpha-L-lyxofuranosyl)adenine, 8-Bromo-9-(5-amino-5-deoxy-1-alpha-L-lyxofuranosyl)adenine, 9-(5,6-Dideoxy-1-beta-D-gulonofuranosyl)adenine, 9-(5,6'-Didehydro-5,6-dideoxy-1-beta-D-gulofuranosyl)adenine, 9-(6'-Amino-5,6-didehydro-5,6'-dideoxy-1-beta-D-gulofuranosyl)adenine, 5-Iodo-4-chloro-7-(1-alpha-L-lyxofuranosyl)pyrrolo[2,3-d]pyrimidine, 5-Bromo-4-chloro-7-(5-deoxy-1-alpha-L-lyxofuranosyl)pyrrolo[2,3-d]pyrimidine, 5-Iodo-4-chloro-7-(5-deoxy-1-alpha-L-lyxofuranosyl)pyrrolo[2,3-d]pyrimidine, 5-Bromo-4-chloro-7-(5-chloro-5-deoxy-1-alpha-L-lyxofuranosyl)pyrrolo[2,3-d]pyrimidine, 5-Iodo-4-chloro-7-(5-chloro-5-deoxy-1-alpha-L-lyxofuranosyl)pyrrolo[2,3-d]pyrimidine, 5-Bromo-4-chloro-7-(5-O-methyl-1-alpha-L-lyxofuranosyl)pyrrolo[2,3-d]pyrimidine, 5-Iodo-4-chloro-7-(5-O-methyl-1-alpha-L-lyxofuranosyl)pyrrolo[2,3-d]pyrimidine, 5-Bromo-4-chloro-7-(5-deoxy-1-beta-D-gulofuranosyl)pyrrolo[2,3-d]pyrimidine, 5-Iodo-4-chloro-7-(5-deoxy-1-beta-D-gulofuranosyl)pyrrolo[2,3-d]pyrimidine, 5-Bromo-4-chloro-7-(5,6-dideoxy-5,6-dideoxy-1-beta-D-gulofuranosyl)pyrrolo[2,3-d]pyrimidine 3-Bromo-4-chloro-1-(1-alpha-L-lyxofuranosyl)pyrazolo[3,4-d]pyrimidine, 3-Bromo-4-chloro-1-(5-deoxy-1-alpha-L-lyxofuranosyl)pyrazolo[3,4-d]pyrimidine, 4-Chloro-3-iodo-1-(1-alpha-L-lyxofuranosyl)pyrazolo[3,4-d]pyrimidine, 4-Chloro-3-iodo-1-(5-deoxy-1-alpha-L-lyxofuranosyl)pyrazolo[3,4-d]pyrimidine, 4-Chloro-3-iodo-1-(5-O-methoxy-1-alpha-L-lyxofuranosyl)pyrazolo[3,4-d]pyrimidine, 4-Phenylamino-3-phenyl-1-(5-deoxy-1-alpha-L-lyxofuranosyl)pyrazolo[3,4-d]pyrimidine, 4-Phenylamino-3-phenyl-1-(5-chloro-5-deoxy-1-alpha-L-lyxofuranosyl)pyrazolo[3,4-d]pyrimidine, 4-Phenylamino-3-phenyl-1-(5-azido-5-deoxy-1-alpha-L-lyxofuranosyl)pyrazolo[3,4-d]pyrimidine, 4-Phenylamino-3-phenyl-1-(5-O-methyl-1-alpha-L-lyxofuranosyl)pyrazolo[3,4-d]pyrimidine, 4-Phenylamino-3-phenyl-1-(5-deoxy-1-beta-D-gulofuranosyl)pyrazolo[3,4-d]pyrimidine, 4-Phenylamino-3-phenyl-1-(5,6-dideoxy-1-beta-D-gulofuranosyl)pyrazolo[3,4-d]pyrimidine, 4-Phenylamino-3-phenyl-1-(5,6-didehydro-5,6-dideoxy-1-beta-D-gulofuranosyl)pyrazolo[3,4-d]pyrimidine, 4-Phenylamino-3-(4-methoxyphenyl)-1-(5-deoxy-1-alpha-L-lyxofuranosyl)pyrazolo[3,4-d]pyrimidine, 4-Phenylamino-3-(4-chlorophenyl)-1-(5-deoxy-1-alpha-L-lyxofuranosyl)pyrazolo[ 3,4-d]pyrimidine, 4-Phenylamino-3-(4-carboxamidophenyl)-1-(5-deoxy-1-alpha-L-lyxofuranosyl)pyrazolo[ 3,4-d]pyrimidine, 4-(4-Methoxyphenylamino)-3-phenyl-1-(5-deoxy-1-alpha-L-lyxofuranosyl)pyrazolo[ 3,4-d]pyrimidine, 4-(4-Chlorophenylamino)-3-phenyl-1-(5-deoxy-1-alpha-L-lyxofuranosyl)pyrazolo[ 3,4-d]pyrimidine, 4-(4-Carboxamidophenylamino)-3-phenyl-1-(5-deoxy-1-alpha-L-lyxofuranosyl)pyrazolo[ 3,4-d]pyrimidine, 4-Phenylamino-3-(2-thienyl)-1-(5-deoxy-1-alpha-L-lyxofuranosyl)pyrazolo[ 3,4-d]pyrimidine, 4-Ethynyl-3-phenyl-1-(5-deoxy-1-alpha-L-lyxofuranosyl)pyrazolo[3,4-d]pyrimidine, 4-Methyl-3-phenyl-1-(5-deoxy-1-alpha-L-lyxofuranosyl)pyrazolo[ 3,4-d]pyrimidine, 4-Ethynyl-5-phenyl-1-(5-deoxy-1-alpha-L-lyxofuranosyl)pyrrolo[ 2,3-d]pyrimidine, 4-Methyl-5-phenyl-1-(5-deoxy-1-alpha-L-lyxofuranosyl)pyrrolo[ 2,3-d]pyrimidine, 4-Amino-3-(2-thienyl)-1-(1-alpha-L-lyxofuranosyl)pyrazolo[ 3,4-d]pyrimidine, 4-Phenylamino-5-iodo-7-(5-deoxy-1-alpha-L-lyxofuranosyl)pyrrolo[ 2,3-d]pyrrolopyrimidine, 4-Phenylamino-5-iodo-7-(1-alpha-L-lyxofuranosyl)pyrrolo[2,3-d]pyrimidine, 4-Phenylamino-5-phenyl-(2,3,5-tri-O-acetyl-1-alpha-L-lyxofuranosyl)pyrrolo[ 2,3-d]pyrimidine, 4-Chloro-5-iodo-7-(5-chloro-5-deoxy-1-alpha-L-lyxofuranosyl)pyrrolo[ 2,3-d]pyrimidine, 4-Chloro-5-iodo-7-(5-deoxy-1-beta-D-gulonofuranosyl)pyrrolo[2,3-d]pyrimidine, 4-Chloro-5-iodo-7-(5,6-didehydro-5,6-dideoxy-1-beta-D-gulonofuranosyl)pyrrolo[2,3-d]pyrimidine, 5-Bromo-4-chloro-7-(5,6-dideoxy-1-beta-D-gulofuranosyl)pyrrolo[ 2,3-d]pyrimidine, 4-Chloro-5-iodo-7-(5,6-dideoxy-1-beta-D-gulofuranosyl)pyrrolo[ 2,3-d]pyrimidine, 5-Iodo-4-(N-phenylamino)-7-(alpha-L-lyxofuranosyl)pyrrolo[ 2,3-d]pyrimidine, 4-(4,5-Difluorophenylamino)-5-phenyl-7-(1-alpha-L-lyxofuranosyl)pyrrolo[ 2,3-d]pyrimidine, 4-(4-Cyanophenylamino)-5-(4-fluorophenyl)-7-(1-alpha-L-lyxofuranosyl)pyrrolo[ 2,3-d]pyrimidine, 4-(4,5-Dichlorophenylamino)-5-phenyl-7-(1-alpha-L-lyxofuranosyl)pyrrolo[ 2,3-d]pyrimidine, 4-(4-Fluorophenylamino)-5-(4-fluorophenyl)-7-(1-alpha-L-lyxofuranosyl)pyrrolo[ 2,3-d]pyrimidine, 4-(4-Phenylamino)-5-(4-fluorophenyl)-7-(1-alpha-L-lyxofuranosyl)pyrrolo[ 2,3-d]pyrimidine, 4-(4-Phenylamino)-5-(4-chlorophenyl)-7-(1-alpha-L-lyxofuranosyl)pyrrolo[ 2,3-d]pyrimidine, 4-(4-Phenylamino)-5-(4-bromophenyl)-7-(1-alpha-L-lyxofuranosyl)pyrrolo[ 2,3-d]pyrimidine, 4-(4-Phenylamino)-5-(4-methoxyphenyl)-7-(1-alpha-L-lyxofuranosyl)pyrrolo[ 2,3-d]pyrimidine, 4-(4-Fluorophenylamino)-5-(4-methoxyphenyl)-7-(1-alpha-L-lyxofuranosyl)pyrrolo[ 2,3-d]pyrimidine, 4-(4-Phenylamino)-5-(4-cyanophenyl)-7-(1-alpha-L-lyxofuranosyl)pyrrolo[ 2,3-d]pyrimidine, 4-(4-Fluorophenylamino)-5-(4-cyanophenyl)-7-(1-alpha-L-lyxofuranosyl)pyrrolo[ 2,3-d]pyrimidine, 4-(4-Phenylamino)-5-(3-nitrophenyl)-7-(1-alpha-L-lyxofuranosyl)pyrrolo[ 2,3-d]pyrimidine, 4-(4-Fluorophenylamino)-5-(3-nitrophenyl)-7-(1-alpha-L-lyxofuranosyl)pyrrolo[ 2,3-d]pyrimidine, 4-(3,5-Difluorophenylamino)-5-phenyl-7-(5-deoxy-1-alpha-L-lyxofuranosyl)pyrrolo[ 2,3-d]pyrimidine, 4-(4-Fluorophenylamino)-5-(4-fluorophenyl)-7-(5-deoxy-1-alpha-L-lyxofuranosyl)pyrrolo[ 2,3-d]pyrimidine, 4-(4-Fluorophenylamino)-5-(4-methoxyphenyl)-7-(5-deoxy-1-alpha-L-lyxofuranosyl)pyrrolo[ 2,3-d]pyrimidine, 4-(4-Cyanophenylamino)-5-phenyl-7-(5-deoxy-1-alpha-L-lyxofuranosyl)pyrrolo[ 2,3-d]pyrimidine, 4-(4-Cyanophenylamino)-5-(4-methoxyphenyl)-7-(5-deoxy-1-alpha-L-lyxofuranosyl)pyrrolo[ 2,3-d]pyrimidine, 4-(4-Pyridylamino)-5-phenyl-7-(5-deoxy-1-alpha-L-lyxofuranosyl)pyrrolo[ 2,3-d]pyrimidine, 4-(3-Pyridylamino)-5-phenyl-7-(5-deoxy-1-alpha-L-lyxofuranosyl)pyrrolo[ 2,3-d]pyrimidine, 4-(2-Pyridylamino)-5-phenyl-7-(5-deoxy-1-alpha-L-lyxofuranosyl)pyrrolo[ 2,3-d]pyrimidine, 4-(4-Fluorophenylamino)-5-phenyl-7-(5-amino-5-deoxy-1-alpha-L-lyxofuranosyl)pyrrolo[ 2,3-d]pyrimidine, 4-(3,5-Difluorophenylamino)-5-phenyl-7-(5-amino-5-deoxy-1-alpha-L-lyxofuranosyl)pyrrolo[ 2,3-d]pyrimidine, 4-(4-Cyanophenylamino)-5-phenyl-7-(5-amino-5-deoxy-1-alpha-L-lyxofuranosyl)pyrrolo[ 2,3-d]pyrimidine, 4-(4-Fluorophenylamino)-5-(4-fluorophenyl)-7-(5-amino-5-deoxy- 1-alpha-L-lyxofuranosyl)pyrrolo[2,3-d]pyrimidine, 4-(3,5-Difluorophenylamino)-3-phenyl-1-(1-alpha-L-lyxofuranosyl)pyrazolo[ 3,4-d]pyrimidine, 4-(4-Fluorophenylamino)-3-(4-fluorophenyl)-1-(1-alpha-L-lyxofuranosyl)pyrazolo[ 3,4-d]pyrimidine, 4-(4-Methoxyphenylamino)-3-(4-fluorophenyl)-1-(1-alpha-L-lyxofuranosyl)pyrazolo[ 3,4-d]pyrimidine, 4-(4-Fluorophenylamino)-3-(4-methoxyphenyl)-1-(1-alpha-L-lyxofuranosyl)pyrazolo[ 3,4-d]pyrimidine, 4-(4-Cyanophenylamino)-3-phenyl-1-(1-alpha-L-lyxofuranosyl)pyrazolo[ 3,4-d]pyrimidine, 4-(4-Cyanophenylamino)-3-(4-fluorophenyl)-1-(1-alpha-L-lyxofuranosyl)pyrazolo[ 3,4-d]pyrimidine, 4-(4-Pyridylmethylamino)-3-bromo-1-(1-alpha-L-lyxofuranosyl)pyrazolo[ 3,4-d]pyrimidine, 4-(2-Pyridylmethylamino)-3-bromo-1-(1-alpha-L-lyxofuranosyl)pyrazolo[ 3,4-d]pyrimidine, 4-(4-Pyridylmethylamino)-3-iodo-1-(1-alpha-L-lyxofuranosyl)pyrazolo[ 3,4-d]pyrimidine, 4-(3-Pyridylmethylamino)-3-iodo-1-(1-alpha-L-lyxofuranosyl)pyrazolo[ 3,4-d]pyrimidine, 4-(4-Pyridylmethylamino)-3-phenyl-1-(1-alpha-L-lyxofuranosyl)pyrazolo[ 3,4-d]pyrimidine, 4-(3-Pyridylmethylamino)-3-phenyl-1-(1-alpha-L-lyxofuranosyl)pyrazolo[ 3,4-d]pyrimidine, 4-(3-Pyridylamino)-5-phenyl-1-(5-deoxy-1-alpha-L-lyxofuranosyl)pyrazolo[ 3,4-d]pyrimidine, 4-(4-Pyridylamino)-5-phenyl-1-(5-deoxy-1-alpha-L-lyxofuranosyl)pyrazolo[ 3,4-d]pyrimidine, 4-(2-Pyridylamino)-5-phenyl-1-(5-deoxy-1-alpha-L-lyxofuranosyl)pyrazolo[ 3,4-d]pyrimidine, 4-(3,5-Difluorophenylamino)-3-phenyl-1-(5-deoxy-1-alpha-L-lyxofuranosyl)pyrazolo[ 3,4-d]pyrimidine, 4-(4-Fluorophenylamino)-3-(4-fluorophenyl)-1-(5-deoxy-1-alpha-L-lyxofuranosyl)pyrazolo[ 3,4-d]pyrimidine, 4-(4-Fluorophenylamino)-3-(4-fluorophenyl)-1-(5-deoxy-1-alpha-L-lyxofuranosyl)pyrazolo[ 3,4-d]pyrimidine, 4-(3-Pyridylmethylamino)-3-phenyl-1-(5-deoxy-1-alpha-L-lyxofuranosyl)pyrazolo[ 3,4-d]pyrimidine, 4-(4-Pyridylmethylamino)-3-phenyl-1-(5-deoxy-1-alpha-L-lyxofuranosyl)pyrazolo[ 3,4-d]pyrimidine, 4-(2-Pyridylmethylamino)-3-phenyl-1-(5-deoxy-1-alpha-L-lyxofuranosyl)pyrazolo[ 3,4-d]pyrimidine, 4-(4-Fluorophenylamino)-3-(4-fluorophenyl)-1-(5-amino-5-deoxy- 1-alpha-L-lyxofuranosyl)pyrazolo[3, 4-d]pyrimidine, and 4-(4-Cyanophenylamino)-3-phenyl-1-(5-amino-5-deoxy-1-alpha-L-lyxofuranosyl)pyrazolo[ 3,4-d]pyrimidine.

More preferred are the following compounds:

4-Amino-5-bromo-7-(5-deoxy-1-alpha-L-lyxofuranosyl)pyrrolo[ 2,3-d]pyrimidine,

4-Amino-5-bromo-7-(1-alpha-L-lyxofuranosyl)pyrrolo [2,3-d] pyrimidine,

4-Chloro-5-iodo-7-(1-alpha-L-lyxofuranosyl)pyrrolo[2, 3-d]pyrimidine,

4-Amino-5-iodo-7-(1-alpha-L-lyxofuranosyl)pyrrolo[2, 3-d]pyrimidine,

5-Bromo-4-chloro-7-(1-alpha-L-lyxofuranosyl)pyrrolo [2,3-d]pyrimidine, 4-(Phenylamino)-5-(2-thienyl)-7-(1-alpha-L-lyxofuranosyl)pyrazolo[ 2,3-d]pyrimidine 5-Iodo-4-(phenylamino)-7-(5-deoxy-1-alpha-L-lyxofuranosyl)pyrrolo[2,3-d]pyrimidine, 4-Amino-5-iodo-7-(5-deoxy-1-beta-D-gulofuranosyl)pyrrolo[2,3-d]pyrimidine, 4-Amino-6-chloro-5-iodo-7-(1-alpha-L-lyxofuranosyl)pyrrolo[ 2,3-d]pyrimidine, 4-Amino-6-chloro-5-iodo-7-(5-deoxy-1-alpha-L-lyxofuranosyl)pyrrolo[ 2,3-d]pyrimidine, 4-Amino-5-bromo-7-(5-amino-5-deoxy-1-alpha-L-lyxofuranosyl)pyrrolo[ 2,3-d]pyrimidine, 6-Chloro-4-(phenylamino)-5-phenyl-7-(5-amino-5-deoxy-1-alpha-L-lyxofuranosyl)pyrrolo[ 2,3-d]pyrimidine, 6-Chloro-4-(phenylamino)-5-phenyl-7-(1-alpha-L-lyxofuranosyl)pyrrolo[ 2,3-d]pyrimidine, 4-(Phenylamino)-5-(4-methoxyphenyl)-7-(5-deoxy-1-alpha-L-lyxofuranosyl)pyrrolo[ 2,3-d]pyrimidine, 4-(4-Methoxyphenylamino)-5-phenyl-7-(1-alpha-L-lyxofuranosyl)pyrrolo[ 2,3-d]pyrimidine, 4-(4-Chlorophenylamino)-5-phenyl-7-(1-alpha-L-lyxofuranosyl)pyrrolo[ 2,3-d]pyrimidine, 4-(4-Methoxyphenylamino)-5-phenyl-7-(5-amino-5-deoxy-1-alpha-L-lyxofuranosyl)pyrrolo[ 2,3-d]pyrimidine, 4-(4-Chlorophenylamino)-5-phenyl-7-(5-amino-5-deoxy-1-alpha-L-lyxofuranosyl)pyrrolo[ 2,3-d]pyrimidine, 4-(4-Methoxyphenylamino)-5-phenyl-7-(5-deoxy-1-alpha-L-lyxofuranosyl)pyrrolo[ 2,3-d]pyrimidine, 4-Amino-3-bromo-1-(1-alpha-L-lyxofuranosyl)pyrazolo [3,4-d]pyrimidine, 4-Amino-3-iodo-1-(5-deoxy-1-alpha-L-lyxofuranosyl)pyrazolo[ 3,4-d]pyrimidine, 4-Amino-3-iodo-1-(5-amino-5-deoxy-1-alpha-L-lyxofuranosyl)pyrazolo[3,4-d]pyrimidine, 4-Phenylamino-3-phenyl-1-(5-amino-5-deoxy-1-alpha-L-lyxofuranosyl)pyrazolo[ 3,4-d ]pyrimidine, 4-(4-Ethoxyphenylamino)-5-phenyl-7-(1-alpha-L-lyxofuranosyl)pyrrolo[ 2,3-d]pyrimidine, 4-(4-Ethylphenylamino)-5-phenyl-7-(1-alpha-L-lyxofuranosyl)pyrrolo[ 2,3-d]pyrimidine, 4-(4-Cyanophenylamino)-5-phenyl-7-(1-alpha-L-lyxofuranosyl)pyrrolo[ 2,3-d]pyrimidine 4-(3-Pyridylamino)-5-phenyl-7-(1-alpha-L-lyxofuranosyl)pyrrolo[ 2,3-d]pyrimidine, 4-(2-Pyridylamino)-5-phenyl-7-(1-alpha-L-lyxofuranosyl)pyrrolo[ 2,3-d]pyrimidine 4-(3-Pyridylmethylamino)-5-iodo-7-(1-alpha-L-lyxofuranosyl)pyrrolo[ 2,3-d]pyrimidine, 4-(2-Pyridylmethylamino)-5-iodo-7-(1-alpha-L-lyxofuranosyl)pyrrolo[ 2,3-d]pyrimidine, 4-(4-Pyridylmethylamino)-5-phenyl-7-(1-alpha-L-lyxofuranosyl)pyrrolo[ 2,3-d]pyrimidine, 4-(3-Pyridylmethylamino)-5-phenyl-7-(1-alpha-L-lyxofuranosyl)pyrrolo[ 2,3-d]pyrimidine, 4-(2-Pyridylmethylamino)-5-phenyl-7-(1-alpha-L-lyxofuranosyl)pyrrolo[ 2,3-d]pyrimidine, 4-(3-Pyridylmethylamino)-3-bromo-1-(1-alpha-L-lyxofuranosyl)pyrazolo[ 3,4-d]pyrimidine, and 4-(2-Pyridylmethylamino)-3-phenyl-1-(1-alpha-L-lyxofuranosyl)pyrazolo[ 3,4-d]pyrimidine.

Most preferred are the following compounds:

4-Amino-5-iodo-7-(5-deoxy-1-alpha-L-lyxofuranosyl)pyrrolo[ 2,3-d]pyrimidine,

5-Phenyl-4-(phenylamino)-7-(1-alpha-L-lyxofuranosyl)pyrrolo[ 2,3-d]pyrimidine,

5-Phenyl-4-(phenylamino)-7-(5-amino-5-deoxy-1-alpha-L-lyxofuranosyl)pyrrolo[ 2,3-d]pyrimidine, 4-Amino-5-iodo-7-(5-amino -5-deoxy-1-alpha-L-lyxofuranosyl)pyrrolo[ 2,3-d]pyrimidine, 5-Phenyl-4-(phenylamino)-7-(5-deoxy-1-alpha-L-lyxofuranosyl)pyrrolo[ 2,3-d]-pyrimidine, 4-Amino-3-bromo-1-(5-deoxy-1-alpha-L-lyxofuranosyl)pyrazolo[ 3,4-d]pyrimidine, 4-Amino-3-bromo-1-(5-amino -5-deoxy-1-alpha-L-lyxofuranosyl)pyrazolo[ 3,4-d]pyrimidine, 4-Amino-3-iodo-1-(1-alpha-L-lyxofuranosyl)pyrazolo[3, 4-d] pyrimidine, 4-Phenylamino-3-phenyl-1-(1-alpha-L-lyxofuranosyl)pyrazolo[ 3,4-d]pyrimidine, 4-(4-Fluorophenylamino)-5-phenyl-7-(1-alpha-L-lyxofuranosyl)pyrrolo[ 2,3-d]pyrimidine, 4-(4-Cyanophenylamino)-5-(4-methoxyphenyl)-7-(1-alpha-L-lyxofuranosyl)pyrrolo[ 2,3-d]pyrimidine, 4-(4-Pyridylamino)-5-phenyl-7-(1-alpha-L-lyxofuranosyl)pyrrolo[ 2,3-d]pyrimidine, 4-(4-Pyridylmethylamino)-5-iodo-7-(1-alpha-L-lyxofuranosyl)pyrrolo[ 2,3-d]pyrimidine, 4-(4-Fluorophenylamino)-5-phenyl-7-(5-deoxy-1-alpha-L-lyxofuranosyl)pyrrolo[ 2,3-d]pyrimidine, 4-(4-Fluorophenylamino)-3-phenyl-1-(1-alpha-L-lyxofuranosyl)pyrazolo[ 3,4-d]pyrimidine, 4-(4-Fluorophenylamino)-3-(3-thienyl)-1-(1-alpha-L-lyxofuranosyl)pyrazolo[ 3,4-d]pyrimidine, and 4-(4-Fluorophenylamino)-3-phenyl-1-(5-deoxy-1-alpha-L-lyxofuranosyl)pyrazolo[ 3,4-d]pyrimidine.

SYNTHESIS OF PREFERRED COMPOUNDS

A. Preparation of Compounds of Formula 1

Compounds of the present invention represented by formula 1 can be prepared as follows:

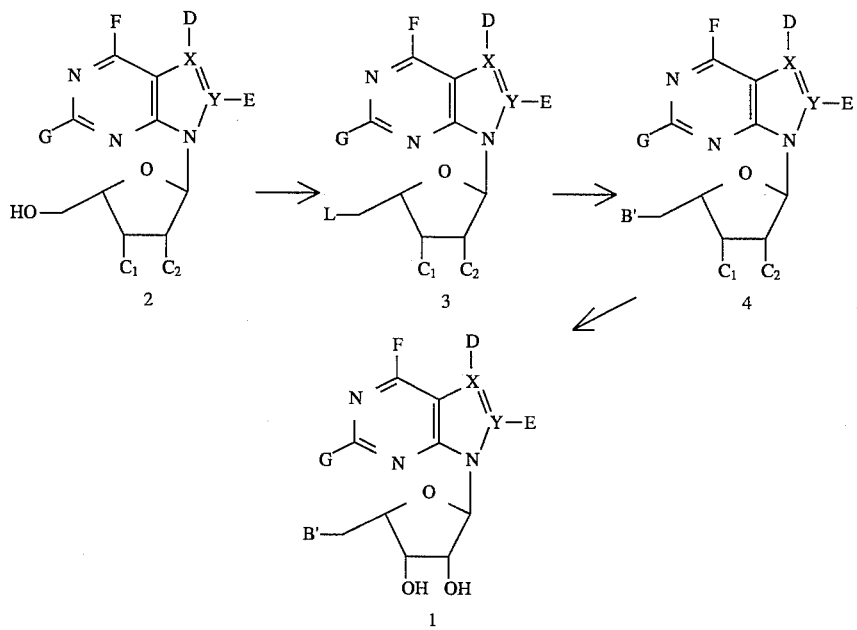

Protecting groups are used throughout the preparation of compounds of the present invention. The purpose of introducing protecting groups is to confine the chemical transformations at the targeted position, e.g. 5'-hydroxyl group, and to protect other functional groups from being affected by the reagents and reaction conditions. The need and choice of protecting groups in both the carbohydrate and heterocycle substituent in 1 for any particular reaction is known to those skilled in the art and depends on the nature of the functional group to be protected, the structure and stability of the molecule of which the substituent is a part, and the reaction conditions. Well known protecting groups that meet these conditions and their introduction and removal are described in the literature (see, e.g. Greene, T. W., Protective Groups in Organic Synthesis, John Wiley & Sons, New York, 1981, pages 10 to 86.)

(i) For compounds where B' is hydrogen, amino, alkylamino, alkoxy, or alkylthio, one process of synthesis involves the use of a starting material of formula 2 where $C_1$ and $C_2$ together are hydroxyls protected by a group well known in the art of protecting 1,2-diols. The 5'-hydroxy group is converted to a leaving group L, e.g. mesylate, rosylate, triflate or a halide, to provide 3. Treatment of 3 with a nucleophile, e.g. hydride, $NR_2$, SR, or OR, or other precursors of amines, such as azides or protected amines, where R is a hydrogen, alkyl, aryl or combination thereof, provides 4, which may be deprotected to give compound 1.

(ii) Compounds of formula 1 where B', D, E, F and G are as defined previously may be prepared by a process which involves coupling of a heterocyclic base of formula 5 and an activated carbohydrate of formula 6.

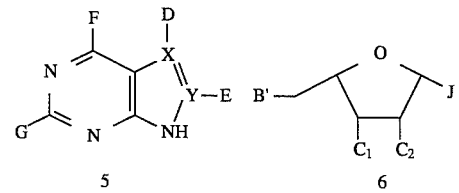

In one instance an alkali metal salt of a heterocyclic base of formula 5, wherein all the substituents are as defined earlier, and a carbohydrate molecule 6 where $C_1$ and $C_2$ are suitably protected hydroxyls, and B' is a hydrogen, alkoxy or a precursor of an amine or a protected amine, and J is a leaving group, e.g. a halogen, preferably chloro, or a sulfonate group are coupled. Alternatively, a heterocycle of formula 5 is coupled to a carbohydrate moiety 6 in which $C_1$ and $C_2$ are acyl protected hydroxyls, preferably acetates, J is an acylated hydroxyl group, preferably acetate. Coupling in this case is carried out using a Lewis acid catalyst, e.g. $BF_3:Et_2O$, $TiCl_4$, $SnCl_4$, TMS-triflate. Removal of the protecting groups and/or converting the amine surrogates to free amines provides the desired final product.

(iii) One preferred method of making a compound of formula 1 where X and Y are carbons, D is a halogen, preferably Br or I; or X is nitrogen, Y is carbon, G and E are hydrogens; and B' and F are amino is by using an intermediate of formula 2 wherein $C_1$ and $C_2$ together are protected (advantageously as isopropylidene) hydroxyls, F is a leaving group, preferably chloro, and D, E and G are as defined above. Reaction of 2 with a sulfonyl chloride electrophile, preferably tosyl chloride in the presence of a base, e.g. NaH or LDA, preferably NaH, provides the intermediate 3. Treating 3 with methanolic ammonia at elevated temperatures produces 4 which is deblocked with an acid, preferably 70% trifluoroacetic acid to provide the desired product 1.

(iv) One preferred method of making compounds of formula 1 where B' is azide, hydrogen, alkoxy, or amino; $C_1$ and $C_2$ are hydroxy; D is a halogen, advantageously Br or I; F is halogen, preferably Cl, or $NR_2$, R being the same as above; X and Y are carbon, G and E are as defined earlier, is by coupling 5 where F is a halogen, preferably chloro, with 6 where $C_1$ and $C_2$ are suitably protected hydroxyls, B' is azide, hydrogen, or alkoxy, and J is chlorine. Nucleophilic reactions of this intermediate with ammonia or substituted amines, e.g. aniline, provide products of formula 1, where F is amino or anilino, respectively after removal of the protecting groups. If desired, the azide function in the 5'-position may be reduced, advantageously with triphenylphosphine and $NH_4OH$ to provide a compound of formula 1 where B' is amino.

(v) One preferred method of making compounds of formula 1 where X is carbon, Y is nitrogen, F is $NR_2$, B' is hydrogen, azido, amino or methoxy, D, E, G, and R are as defined before, is by coupling a heterocycle 5 with the same substituents as above, with carbohydrate 6 where B' is either hydrogen, azido or methoxy, $C_1$ and $C_2$ are protected hydroxyls, preferably as acetyls, J is acylated hydroxyl, preferably as an acetate, using a Lewis acid catalyst, advantageously $BF_3:Et_2O$. Removal of protecting groups provide the product. Where B' is azido, reduction of the azide is carried out, preferably with triphenylphosphine and $NH_4OH$, to provide the appropriate amine.

(vii) A preferred method of making pyrrolopyrimidine compounds of formula 1 where B' is hydrogen, hydroxy, or alkoxy (preferably methoxy); D is aryl; and F is $NR_2$ or halogen, preferably chloro; is by reacting a compound of formula 1 wherein D is halogen and all other groups as above with an arylboronic acid and palladium or nickel complex and a base such as sodium or potassium carbonate. When F is halogen, displacement with ammonia or substituted amine will provide the desired product. Alternatively arylation can proceed with the hydroxyl groups on positions 2', 3', and/or 5' protected as acetates, silyl ethers, isopropylidenes, and the like. Deprotection then provides the desired product. In place of arylboronic acids, organometallics such as aryl zinc, aryl mercury, aryl stannanes, and the like can be used with the hydroxyls of the intermediate compound protected for compatibility with the organometallic used. (Flynn, B. L. et al., *Nucleotides and Nucleosides,* 1991, 10, 763–779). Alternatively the organometallic can consist of a compound of formula 1, where B and F are as previously defined and where D is a substituted metal or boron atom. Arylation then proceeds using an aryl halide or triflate (Bergstrom, D. E., et al., *J. Org. Chem.,* 1991, 56, 5598–5602).

B. Preparation of Compounds of Formula 2

Compounds of formula 2 can be made by the following processes:

(i) A compound of formula Z where $C_1$ and $C_2$ are hydroxy, D is halogen, preferably bromo or iodo, or aryl, including heteroaryl; F is chloro or $NR_2$ where R is hydrogen, alkyl, aryl, aralkyl, or any combination thereof; and G, E, X and Y are as defined earlier, can be prepared by coupling a heterocycle 5 containing the same substitutents as above, with a carbohydrate 6 where $C_1$ and $C_2$ are protected hydroxyls, B' and J are hydroxy groups protected independently with different groups that are stable to the reaction conditions, e.g. in the presence of Lewis acid catalysts, known in the art for coupling such purine analogs to various ribose analogs (Lerner, L. M., *Carbohydrate Res.,* 1988, 184, 250–253). Removal of the protecting groups from the resulting product provides the product 2.

(ii) Alternatively, these compounds can be made by coupling alkali metal salts of heterocycles of formula 5 bearing same substituents as above, with 6 where B' is protected hydroxy, advantageously as a tert-butyldimethylsilyl ether, $C_1$ and $C_2$ are protected hydroxyls, preferably with isopropylidene, and J is a leaving group, advantageously chlorine, by following a procedure identical to the one described earlier.

(iii) Another process by which compounds of formula 2 with the same substituents as defined in the above process, using an intermediate of formula 7 as the starting material, where D, E, F and G are as defined above and $C_1$ and $C_2$ are protected hydroxyls, preferably as isopropylidene. Compound 7 is hydroxylated, for example by hydroboration, with one of many hydroborating agents known in the art and finally removal of the blocking groups provides product 2.

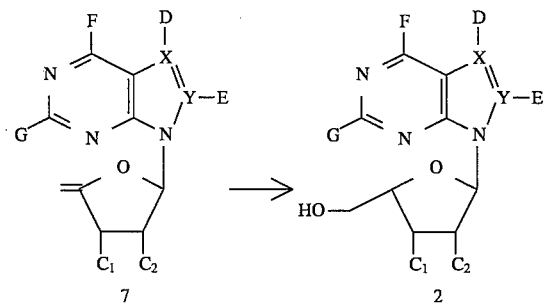

(iv) Another process by which compounds of formula 2 can be made is by isomerizing the easily accessible ribofuranosyl analog 8 to its lyxofuranosyl form as shown below:

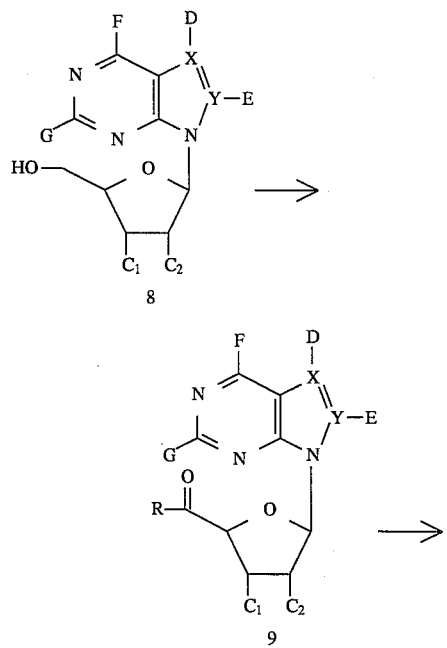

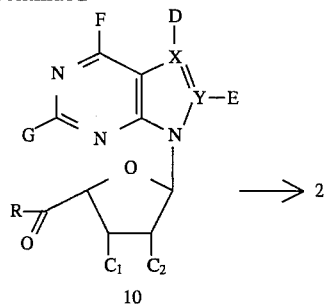

R = H, OR, R'

Typically, a ribose analog of formula 8 where D, E, F, G, X, and Y are as defined before and, $C_1$ and $C_2$ are suitably protected hydroxyls, is oxidized by a reagent known in the art to oxidize hydroxyl groups to produce an acid or aldehyde 9. The resulting carbonyl compound 9 is treated with a base under conditions known in the art to cause enolization and epimerization at the C-4 carbon atom of the carbohydrate ring to provide 10. Reduction of 10 with reducing agents such as LAH or $NaBH_4$, advantageously $NaBH_4$, provides the target molecule 2.

(v) A preferred procedure to make compounds of formula 2 where X and Y are carbon, D is a halogen, e.g. bromo or iodo, F is $NH_2$, $C_1$ and $C_2$ are hydroxy, and G and E are as defined before, is to treat heterocycle 5 where F is a leaving group, especially a chloro, and the rest of the substituents the same as above, with a compound of formula 6 where $C_1$ and $C_2$ are protected hydroxyls, preferably as isopropylidene' B' is protected hydroxyl, preferably as tert-butyldimethylsilyl ether; and J is a leaving group, advantageously chlorine. Typically, the sodium salt of heterocycle 5 is generated by treatment with a strong base in an inert solvent, preferably sodium hydride in acetonitrile. A solution of 6 is added and the mixture stirred overnight to obtain the blocked nucleoside intermediate. Deblocking with an acid, preferably with 70% trifluoroacetic acid provides 11, which upon treatment with methanolic ammonia at elevated temperatures gives the desired product.

(vi) Another preferred method of making compounds of formula 2 where x is a carbon and Y is a nitrogen is to couple a preformed heterocycle of formula 5 where D is aryl or halogen, advantageously iodo or bromo, and the other substituents as above, with a carbohydrate 6 where $C_1$ and $C_2$ are independently protected hydroxyls, advantageously benzoyls, B' is a suitably protected hydroxyl, preferably benzoate, and J is an acylated hydroxyl group, especially acetate, using a Lewis acid catalyst, preferably $BF_3:Et_2O$, in a suitable solvent such as nitromethane. The product is deprotected with a base, especially with methanolic sodium methoxide, to provide the desired product.

(vii) Another preferred method of making a compound of formula 2, where X is nitrogen, Y is carbon, F is $NH_2$, $C_1$ and $C_2$ are hydroxy, G and E are hydrogen, B' is hydroxyl, is by coupling a heterocycle of formula 5 where E, F, G, X and Y are the same as above, with a compound of formula 6. In compound 6, B' and J are suitably protected hydroxyls, advantageously J as acetate and B' as benzoate, and $C_1$ and $C_2$ are independently protected hydroxyls, especially benzoyls. The coupling may be done in an inert solvent, advantageously $CH_3CN$, in presence of a Lewis acid catalyst, preferably $SnCl_4$. The product is deprotected with a base, such as sodium methoxide in methanol, to provide the desired product.

(viii) Pyrrolopyrimidine and pyrazolopyrimidine compounds of formula 2 wherein $C_1$ and $C_2$ are hydroxyls, D is an aryl group, and F is $NR_2$ where R is defined as before, can also be prepared by using an intermediate also of formula 2 where D is halogen, and the other substituents are as before. This intermediate can be coupled to an aryl group, such as phenyl or a heteroaryl ring such as thiophenyl, furanyl, pyridyl, in a manner as described earlier in paragraph B(vii).

(ix) A preferred procedure to make compounds of formula 2 where F is an arylamino group, especially anilino, D is aryl, X and Y are carbon, and the remaining substitutents are as in the previous case, is by condensing a compound of formula 11 where F is chloro, D is halogen, preferably Br or I, with aniline. The product is treated with an aryl boronic acid, a Pd(O) catalyst, advantageously tetrakis(triphenylphosphine)palladium and a base, preferably potassium carbonate, to provide the product.

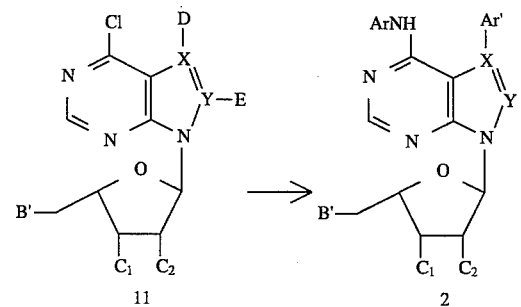

C. Preparation of Intermediates of Formula 6

(i) Compounds of formula 6 where B' is a protected hydroxyl such that the protecting group may be removed selectively without affecting the protecting groups attached to $C_1$ and $C_2$ hydroxyls, preferably as a silyl ether, advantageously as a tert-butyldimethylsilyl ether; $C_1$ and $C_2$ are suitably protected hydroxyls, preferably an isopropylidene group; J is halogen, preferably chlorine, can be prepared from commercially available L-lyxose.

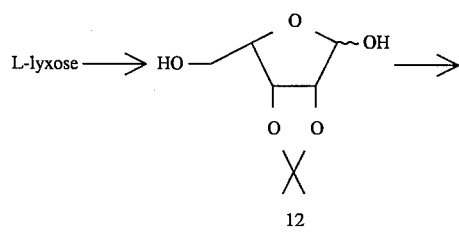

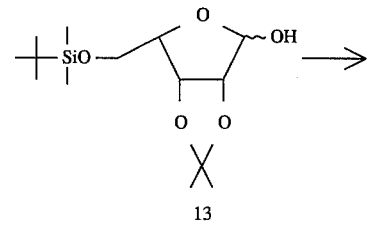

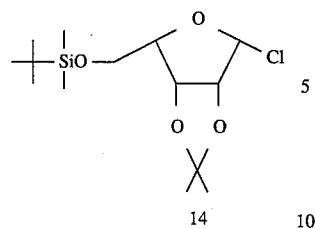

Treatment of L-lyxose with reagents known to protect diols as isopropylidene, (e.g. acetone or acetone-triethylorthoformate mixtures) in presence of an suitable acid catalyst, preferably p-toluenesulfonic acid, provides an intermediate 12. The 5-hydroxy group of 12 can be converted into a silyl ether, preferably tert-butyldimethylsilyl ether, by treatment with an appropriate silyl chloride or bromide, preferably chloride, in presence of a base, preferably imidazole, to give 13. Conversion of the 1-hydroxy group to 1-chloro can be accomplished by treatment with a number of reagents that are known in the art of making 1-halosugars, e.g. anhydrous HCl in an inert solvent, thionyl chloride, preferably carbon tetrachloride and HMPT at −78° C., to provide the final chloro compound 14.

(ii) One preferred procedure of making compounds of formula 6 where B' is a protected hydroxyl, advantageously as tert-butyldimethylsilyl ether, $C_1$ and $C_2$ together are hydroxyls, protected by a group that is known in the art for protecting diols, preferably isopropylidene, and J is a halogen, advantageously a chloro, is to treat L-lyxose with 2,2-dimethoxypropane and catalytic amount of p-toluenesulfonic acid to obtain 12. The 5-OH group of 12 is protected by treatment with tert-butyldimethylsilyl chloride in the presence of a base such as imidazole to provide 13, which is converted to its chloro derivative 14, with carbon tetrachloride and HMPT at −78° C.

(iii) A compound of formula 6 where B' and J are hydroxyls protected as acyl esters, and $C_1$ and $C_2$ are acyl protected hydroxyls, can be prepared from L-lyxose. L-lyxose is first converted to its 1-O-alkyl or 1-O-aralkyl derivative 15 by treatment with an alkanol, e.g. methanol, ethanol or arylalkanol, e.g. benzyl alcohol, advantageously methanol and an acid, preferably HCl. Acylation of this intermediate with acylating agents that are known to the art of acylating the alcoholic functions, e.g. acid chlorides such as acetyl chloride, or acid anhydrides such as benzoic anhydride or acetic anhydride, in the presence of a base, preferably pyridine, provides 1-O-alkyl-2,3,5-tri-O-acyl-L-lyxose derivative 16. Converting 1-O-alkyl group to a 1-O-acyl group can be accomplished by either first converting it to 1-OH derivative with a strong acid and then acylating it, or acylation of 16 directly under strongly acidic conditions to obtain the desired product 17.

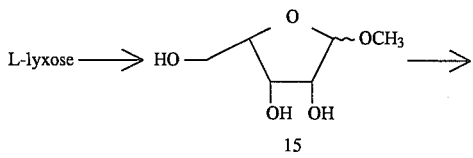

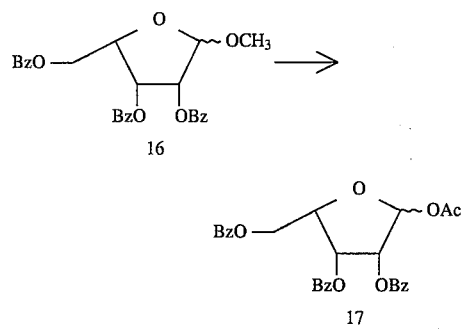

The preferred method of making 6 where B' and J are hydroxyl groups protected as acyl esters, advantageously B' is benzoate, and J is acetate, and $C_1$ and $C_2$ are protected hydroxyls, preferably benzoates, involves treatment of L-lyxose to 15 with methanolic hydrogen chloride. The product is benzoylated with benzoic anhydride and pyridine to obtain 16 which can be acetylated with acetic anhydride under strongly acidic conditions, preferably a mixture of acetic acid and concentrated sulfuric acid, to provide the desired product 17.

(iv) Compounds of formula 6, where B' is hydrogen, $C_1$ and $C_2$ are suitably protected hydroxyls, advantageously protected as isopropylidene, and J is halogen, preferably chloro, can be made from compound 18 which can be made by the literature procedure (Hough et al., Adv, Chem. Ser., 1968, 74, 120–140). Catalytic hydrogenation of compound 18 by procedures known in the art for reducing olefins or enol ethers, provides protected intermediate 19. Such an intermediate can be converted to 21 either by selective demethylation, by procedures known in the art of demethylating 1-O-methyl glycosides, or by removing all protecting groups under conditions known in the art of removing the acid labile protecting groups such as ketals and acetals, advantageously with dilute aqueous sulfuric acid at elevated temperatures, to provide 20. It is further converted to 21 using reagents known in the art of protecting 1,2-diols, preferentially as isopropylidene. Chlorination of 21 can be accomplished by procedures known to convert the 1-hydroxy groups of sugar derivatives to 1-chloro derivatives, preferably carbon tetrachloride and HMPT at low temperatures.

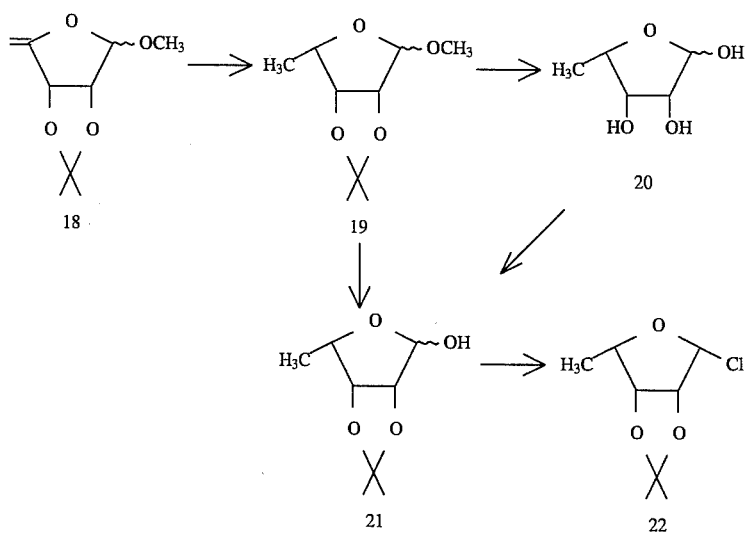

(v) Alternatively compound of formula 22 can be obtained by hydroborating 18 with hydroborating agents known in the art, advantageously, diborane, and refluxing intermediate 23 with high boiling carboxylic acids, advantageously propionic acid, to provide an intermediate of formula 20 and/or 21. The intermediates thus obtained can be converted to the desired product by a procedure already specified.

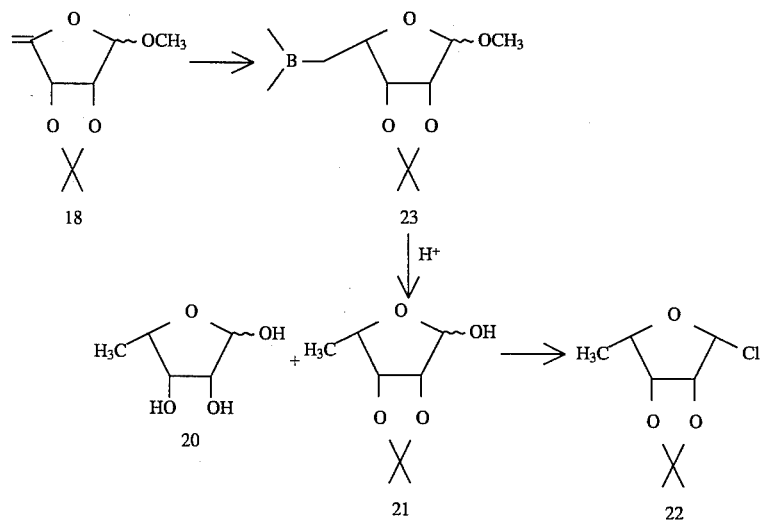

(vi) Another process to prepare compounds of formula 21 begins with D-ribose. The 2-and 3-hydroxyls are suitably protected, preferably as isopropylidene, and the hydroxyl group in position 1 is protected with a group that can be removed by catalytic hydrogenation, advantageously benzyl, to obtain 26. The 5-hydroxyl is converted into a leaving group such as a sulfonate, e.g. tosylate, mesylate, triflate, or a halogen, preferably iodo, and the product treated with base to cause elimination, advantageously sodium methoxide in methanol at elevated temperatures, to obtain 28. Catalytic hydrogenation provides 21.

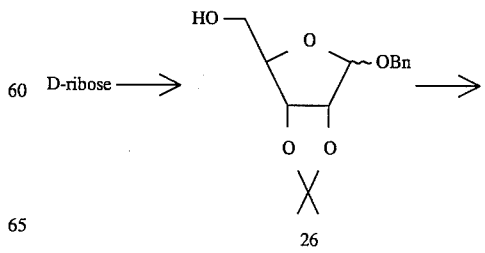

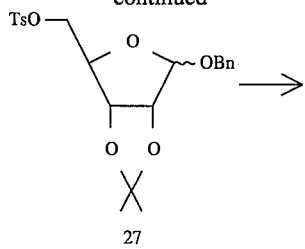

27

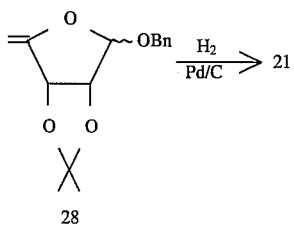

28

(vii) Alternatively compound of formula 22 can be made via 19 from L-lyxose. The 1, 2 and 3 hydroxyls of L-lyxose are protected by groups known in the art of protecting the similar groups in the ribose series, advantageously methyl in 1-position and isopropylidene at positions 2 and 3. (Kiss et al.; Carbohydrates, Nucleosides, Nucleotides, 1980, 7, 141–157). The 5-hydroxy of intermediate 24 is converted to a suitable leaving group, preferably tosylate, and the resulting product 25 is subjected to a reduction process known to reduce sulfonate esters of alcohols, advantageously lithium aluminum hydride, to obtain 19 which could be converted to 22 by a procedure mentioned earlier.

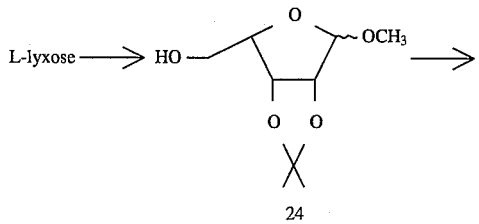

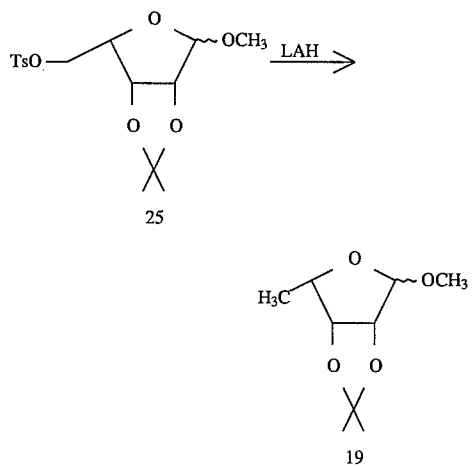

(viii) A preferred method of making compound 6 where B' is hydrogen, J is chloro and $C_1$ and $C_2$ are protected hydroxyls, preferably as isopropylidene, is via compound 18 which can be made by a literature procedure (Inokawa, et al., Carbohydrate Res., 1973, 30, 127–132). High pressure catalytic hydrogenation of 18, advantageously with palladium on carbon, provides 19. The protecting groups are removed under acidic conditions, preferably dilute aqueous sulfuric acid at elevated temperature, giving 20. The hydroxy groups in the positions 2 and 3 are blocked by an appropriate protecting group, preferably isopropylidene, and the product, 21, is chlorinated, preferably with carbon tetrachloride and HMPT, to give 22.

D. Preparation of Compounds of Formula 5

(i) Pyrrolo Pyrimidine Compounds

Heterocyclic aglycons of formula 5 where X and Y are carbon; F is chloro; D is a halogen, preferably Br or I, and G and E are hydrogen, can be made by literature procedures (Pudlo, et al., J. Med. Chem., 1990, 33, 1984–1992; Gerster et al., J. Heterocycl. Chem., 1969, 6, 207–213).

(ii) Pyrazolo Pyrimidine Compounds

Heterocyclic aglycons of formula 5 where X is a carbon; Y is a nitrogen; D is a halogen; F is amino; and G is a hydrogen are made by literature procedure (Leonova, T. et al, Khim. Get. Soed., 1982, 982).

Heterocyclic aglycons of formula 5 where X is a carbon; Y is nitrogen; D is aryl, F is amino, and G is hydrogen, can be made by a literature procedure (Ref: Kobayashi, S. et al., Chem. Pharm. Bull. (Jap), 1973, 21, 941).

Heterocyclic aglycons of formula 5 where X is carbon; Y is nitrogen; D is aryl, F is arylamino, with G and E as defined above, can be made by treating a heterocycle of formula 5 where F is a leaving group (such as a halogen, methylthio, methylsulfonyl) known in the art suitable for nucleophilic displacement, all other groups being the same as above, with an aryl amine at elevated temperatures.

The preferred method of making a compound of formula 5 where X is carbon, Y is nitrogen, D is aryl, preferably phenyl or 2-thienyl, F is phenylamino, and G and E as defined above, is by treating compound 5 where F is chloro and all other groups being the same as above, with ethanolic aniline in a bomb at 110° C.

UTILITY

The adenosine kinase inhibitors of the present invention may be used in the treatment of a variety of clinical situations where increasing local levels of adenosine are beneficial. In particular, these compounds may be used in treating cardiovascular disorders in which injury or dysfunction is caused by ischemia and/or reperfusion (following a period of ischemia). These include (1) heart attack, a situation that arises from obstruction of one or more of the coronary arteries supplying blood to the heart muscle, and which, if prolonged, leads to irreversible tissue damage; (2) angina pectoris, a clinical condition in which the blood supply to the heart is sufficient to meet the normal needs of the heart but insufficient when the needs of the heart increase (e.g. during exercise), and/or when the blood supply becomes more limited (e.g. during coronary artery spasm); (3) unstable angina associated with pain at rest; and (4) silent ischemia. In each of these conditions, treatment with adenosine kinase inhibitors will increase local levels of adenosine. Blood flow to the ischemic tissue would be increased, tissue damage reduced and function improved. Further, compounds of the present invention may also be used to treat or prevent congestive heart failure.

In advanced coronary artery disease or persistent chest pain at rest, a number of clinical procedures are currently used to improve blood supply to the heart. These include percutaneous transluminal coronary angioplasty (PTCA), percutaneous transluminal directional coronary atherectomy, laser atherectomy, intravascular stents and coronary artery bypass graft surgery. The compounds of this invention will also be useful as adjunctive therapies to these techniques. Other clinical settings that involve ischemia would also be ameliorated by agents effecting regional blood flow including organ transplantation, skin flap grafting and other reconstructive surgery, peripheral vascular disease, sepsis, endotoxemia, hemorrhagic shock, pulmonary emboli, pulmonary injury secondary to burns (thermal injury) or septicemia, pulmonary hypertension, microembolization, glomerulonephritis or progressive glomerulosclerosis, atherosclerosis, myocarditis, vasculitis, cardiomyopathies, intestinal ischemia, peripheral vascular disease, transient ischemic attacks, stroke and cardiopulmonary arrest. Adenosine kinase inhibitors will also enhance protection of tissue after a brief period of ischemia before the recurrence of a prolonged period of ischemia.

Thrombolytic therapy has been limited by a number of factors including the resistance of some thrombi to lysis, delays in reperfusion, and reocclusion following successful thrombolysis. These limitations are believed to be mediated, in part, by platelet aggregation and, since adenosine inhibits platelet aggregation in addition to its other effects on preventing ischemic injury, use of these adenosine kinase inhibitors may comprise a useful adjunctive therapy for thrombolytic therapy or for the treatment or prevention of thrombotic diseases such as myocardial infarction, stroke, angina, deep vein thrombosis, transient ischemic attacks, and pulmonary embolus.

Adenosine has been reported to be an endogenous modulator of inflammation by virtue of its effects on stimulated granulocyte function and on macrophage, lymphocyte and platelet function. Adenosine kinase inhibitors of the present invention may be useful in the treatment of disorders of the immune system, in particular inflammatory disorders and advantageously in the treatment of sepsis, septicemia or endotoxemia. Further, these compounds may be used in treating conditions such as arthritis, osteoarthritis, autoimmune disease, adult respiratory distress syndrome (ARDS), inflammatory bowel disease, necrotizing enterocolitis, chronic obstructive pulmonary disease (COPD), psoriasis, conjunctivitis, iridocyclitis, myositis, cerebritis, meningitis, dermatitis, renal inflammation, ischemia, reperfusion injury, peripheral vascular disease, atherosclerosis and other inflammatory disorders.

Stroke and central nervous system ("CNS") trauma are conditions where tissue injury results from reduced blood supply to the CNS and are thus amenable to an intervention that provides increased levels of adenosine to the compromised tissue. A significant component of the neurodegeneration resulting from stroke or CNS trauma or neurodegenerative diseases may be caused by increased excitatory amino acid release which results in neurons being stimulated to death. As adenosine has been reported to inhibit excitatory amino acid release (Burke and Nadler *J. Neurochem.*, 1988, 51: 1541), compounds of this invention may be used in stroke and trauma and may also be used in the treatment of conditions such as Parkinson's disease, Amyotrophic Lateral Sclerosis, Huntington's chorea or Alzheimer's disease or in the treatment of disorders related to the effects of the aging process on CNS function such as Alzheimer's disease or in treating schizophrenia.

These adenosine kinase inhibitors may also be useful in reducing anxiety, as skeletal muscle relaxants and in preventing skeletal muscle spasm.

As adenosine has been proposed to serve as a natural anticonvulsant, thus agents that enhance adenosine levels may be used in the treatment of seizure disorders. Adenosine kinase inhibitors may be used in the treatment of patients prone to seizures or epilepsy or who might have chronic low or insufficient adenosine levels or might benefit from increased adenosine such as those suffering from autism, cerebral palsy, insomnia or other neuropsychiatric symptoms. Other excitatory neuromuscular tissues such as smooth muscle and cardiac muscle may be treated using these adenosine kinase inhibitors. In particular, these adenosine kinase inhibitors may be used to decrease contraction in smooth muscle such as in the gastrointestinal tract, or in vascular tissue such as an artery to prevent vasospasm which may limit blood supply to a tissue. Thus, these adenosine kinase inhibitors may be used to treat conditions such as Buerger's disease, Raynaud's disease, thromboangiitis obliterans, angina, unstable angina, silent ischemia, or transient ischemic attacks. Other conditions suitable for such therapy include cardiac arrhythmias (including supraventricular tachycardia), irritable bowel syndrome, and impotence.

Adenosine kinase inhibitors find further utility in the treatment of chronic and acute pain when administered in a systemic or oral fashion. Compounds of the present invention are useful in controlling chronic pain including but not limited to pain caused by arthritis, cancer, trigeminal neuralgia, multiple sclerosis, neuropathies such as those arising from diabetes and AIDS and in addition, lower back pain and phantom limb pain.

To assist in understanding the present inventions and especially their properties and utilities, the results of a series of experiments are also included. These experiments demonstrate that a number of compounds of Formula A were potent inhibitors of a purified cardiac adenosine kinase with $IC_{50}$'s of less than 1 µM ($IC_{50}$ is defined as the concentration of drug necessary to inhibit 50% of enzyme activity). Moreover, we have shown that these compounds are specific inhibitors of adenosine kinase with low affinity at the $A_1$ adenosine receptor and no significant adenosine deaminase (ADA) inhibition (Example A). Furthermore, We have demonstrated that a number of these compounds are also inhibitors of adenosine kinase in intact cells (Example B). These compounds include 4-amino-5-iodo-7-(1-alpha-L-lyxofuranosyl)pyrrolo[2,3-d]pyrimidine (compound A), 4-(phenylamino)-5-phenyl-7-(1-alpha-L-lyxofuranosyl)pyrrolo[2,3-d]pyrimidine (compound B), and 4-amino-5-iodo-7-(5-amino-5-deoxy-1-alpha-L-lxyofuranosyl)pyrrolo[2,3-d]pyrimidine (compound C).

We have demonstrated that compounds of the presnt invention inhibit adenosine kinase not only in vitro (Example A) but also in vivo (Example C).

We have demonstrated the ability of these compounds to reduce damage resulting from ischemia and/or reperfusion in an experimental ischemic heart model as shown in Example D.

We have further demonstrated the ability of these compounds to be of benefit in the treatment of chronic arthritis (Example E). Surprisingly, compounds of the present invention decreased joint destruction in a model of adjuvant arthritis and thus compounds of the present invention represent an advance over presently available treatments which, although they decrease inflammation, do not prevent joint destruction.

FORMULATIONS

Compounds of the invention are administered to the affected tissue at the rate of from 0.1 to 200 nmol/min/kg, preferably from 1 to 20 nmol/min/kg. Such rates are easily maintained when these compounds are intravenously administered as discussed below. When other methods are used (e.g., oral administration), use of time-release preparations to control the rate of release of the active ingredient may be preferred. These compounds are given in a dose of about 0.01 mg/kg/day to about 100 mg/kg/day, preferably from about 0.1 mg/kg/day to about 10 mg/kg/day.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections for the treatment of myocardial infarction. When an organ outside a body is being treated, perfusion is preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservative such as ethyl or n-propyl p-hydroxybenzoate, one or more coloring agent, one or more flavoring agent and one or more sweetening agent, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 200 μmoles of active material compounded with an appropriate and convenient amount of carrier material which may vary from about 5 to about 95% of the total compositions. It is preferred that pharmaceutical composition be prepared which provides easily measurable amounts for administration. For example, an aqueous solution intended for intravenous infusion should contain from about 20 to about 50 µmoles of the active ingredient per milliliter of solution in order that infusion of a suitable volume at a rate of about 30 ml/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach. This is particularly advantageous with the compounds of formula A as such compounds are susceptible to acid hydrolysis.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the ddPN ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be sorted in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, of an adenosine kinase inhibitor compound.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Examples of use of the method of the invention includes the following. It will be understood that these examples are exemplary and that the method of the invention is not limited solely to these examples.

The method may be used following thrombolysis for coronary occlusion. The compound would be given as a sterile injectable preparation with water or isotonic sodium chloride as the solvent. The solution can be administered intravenously or directly into the coronary artery at the time of left heart catheterization or into a carotid artery. The rate of administration could vary from 1 to 20 nmole/min/kg with, for example, an infusion volume of 30 ml/hr. Duration of therapy would typically be about 96 hours.

Angina and early myocardial infarcts can be treated by intravenous administration using a sterile injectable preparation using the rates discussed above.

Capsules comprising adenosine kinase inhibitors suitable for oral administration according to the methods of the present invention may be prepared as follows: (1) for a 10,000 capsule preparation: 1500 g of adenosine kinase inhibitor is blended with other ingredients (as described above) and filled into capsules which are suitable for administration depending on dose, from about 1 capsule per day to about 8 capsules per day (2 capsules per 6 hours), to an adult human.

The compounds of this invention and their preparation can be understood further by the examples which illustrate some of the processes by which these compounds are prepared. These examples should not however be construed as specifically limiting the invention and variations of the invention, now known or later developed, are considered to fall within the scope of the present invention as herein after claimed.

EXAMPLES

Example 1

Preparation of 2,3-Isopropylidene-L-lyxofuranose

A mixture of L-lyxose (10.0 g, 67 mmol) 100 mL of DMF, 2,2-dimethoxypropane (20 mL) and p-toluenesulfonic acid (150 mg) was stirred for 3 hours. The solvent was removed and the residue was chromatographed to obtain 2,3-isopropylidene-L-lyxofuranose as a colorless oil. Yield was 12.0 g.

Example 2

Preparation of 2,3-Isopropylidene-5-tert-butyldimethylsilyl-L-lyxofuranose

To a solution of imidazole (4.2 g, 63 mmol) and 2,3-isopropylidene-L-lyxofuranose (10.0 g) in 1.75 L of $CH_2Cl_2$ at 0° C. was added a solution of TBDMSCl (8.72 g, 58 mmol) in 100 mL of $CH_2Cl_2$ over 1 hour. After 3 hours, the mixture was extracted with water. The organic layer was separated, dried and evaporated to obtain the title compound as an oily product. Yield was 12.8 g.

Example 3

Preparation of 4-Chloro-5-iodo-7-(5-tert-butyldimethylsilyl-2,3-isopropylidene-1-α-L-lyxofuranosyl)pyrrolo[2,3-d]pyrimidine To a solution of 2,3-isopropylidene-5-tert-butyldimethylsilyl-L-lyxofuranose (2.0 g, 6.5 mmol) and $CCl_4$ (1.0 mL) in 35 mL of THF at −78 °C. was slowly added a solution of HMPT (1.4 mL) in 5 mL of THF. The mixture was allowed to warm to −30 °C., stirred for 30 minutes, cooled again to −78 °C. and stirred for 2 hours, to give the lyxofuranosyl chloride which was used directly in the following step.

To a suspension of sodium hydride (0.36 g, 60% in oil) in 30 mL of acetonitrile at 0 °C. was added 4-chloro-5-iodopyrrolo[2,3-d]pyrimidine (2.2 g) over 5 minutes. The cooling bath was removed and stirring was continued for 30 minutes. A solution of previously made chlorosugar was added and the mixture stirred overnight at room temperature. The solvent was removed and the residue was dissolved in 100 mL of EtOAc, filtered through Celite®, concentrated and chromatographed to yield the product, 2.29 g.

Example 4

Preparation of 5-Bromo-4-chloro-7-(2,3-isopropylidene-5-O-tert-butyldimethylsilyl-1-α-L-lyxofurenosyl)pyrrolo[2,3-d]pyrimidine The title compound was made following a procedure similar to that of the corresponding 5-iodo derivative.

Example 5

Preparation of 4-Chloro-5-iodo-7-(2,3-isopropylidene-1-α-L-lyxofuranosyl)pyrrolo[2,3-d]pyrimidine To a solution of product of Example 3 (2.1 g) in 30 mL of THF was added a solution of tetrabutylammonium fluoride in THF (2 mL of 1M solution). The mixture was stirred at room temperature for 30 minutes, the solvent removed and the residue chromatographed to yield 1.3 g of product.

Example 6

Preparation of 4-Amino-5-iodo-7-(1-α-L-lyxofuranosyl)pyrrolo[2,3-d]pyrimidine A solution of product of Example 3 (1.25 g) in 10 mL of 70% trifluoroacetic acid was warmed to 40° C. for 30 minutes. The solvent was removed by coevaporation with water (3×10 mL) and ethanol (1×10 mL). The product was triturated with ethanol (5 mL), the solid collected, washed with cold ethanol and dried to give 0.4 g. The mother liquid was concentrated and cooled to obtain additional product, 0.2 g. A solution of this compound in concentrated methanolic ammonia (15 mL) was heated in sealed bomb at 105° C. for 12 hours. The bomb was cooled, excess ammonia allowed to evaporate and the residue was crystallized from methanol to give 105 mg of product, mp 236°–238° C.

Example 7

Preparation of 4-Amino-5-bromo-7-(1-α-L-lyxofuranosyl)pyrrolo[2,3-d]pyrimidine The title compound was made following the procedure used for the corresponding 5-iodo derivative, mp 129°–132° C.

Example 8

Preparation of 4-Chloro-5-iodo-7-(2,3-isopropylidene-5-O-p-toluenesulfonyl-1-α-L-lyxofuranosyl)pyrrolo[2,3-d]pyrimidine To a suspension of sodium hydride (0.130 g, 80% in oil) in 25 mL of THF at 0° C. was added a solution of the product of example 5 (1.4 g, 4 mmol) in 10 mL of THF. The cooling bath was removed, the mixture was stirred at room temperature for approximately 20 minutes, and a solution of p-toluenesulfonyl chloride (0.95 g, 4.8 mmol) in 10 mL of THF added over 15 minutes. The mixture was stirred overnight, the solvent removed and the residue was chromatographed to yield the title compound, 0.4 g.

Example 9

Preparation of 4-Amino-5-iodo-7-(5-amino-5-deoxy-1-α-L-lyxofuranosyl)pyrrolo[2,3-d]pyrimidine A cooled solution of product of example 8 (400 mg) in 10 mL of methanol saturated with ammonia was heated in a bomb at 100° C. for 8 hours. The bomb was cooled, opened and the unreacted ammonia was allowed to evaporate. The residue was triturated with ether to obtain an off-white solid which was dissolved in 10 mL of 70% trifluoroacetic acid and warmed to 40° C. for 0.5 hour. The solvent was removed, coevaporated with water (3×15 mL) and with methanol (1×10 mL). The mixture was chromatographed on Dowex 50×8 resin to give the product, 105 mg, mp 189°–192° C.

Example 10

Preparation of 4-Amino-5-bromo-7-(5-amino-5-deoxy-1-α-L-lyxofuranosyl)pyrrolo[2,3-d]pyrimidine The title compound was synthesized following a procedure analogous to the synthesis of the corresponding 5-iodo derivative as described in Example 9, 5 mg, Rf=0.45 (silica gel, butanol:acetic acid:water, 4:1:1), mass spectrum, $M^+$=368.

Example 11

Preparation of 4-Chloro-3-phenylpyrazolo[3,4-d]pyrimidine

A mixture of 3-phenylallopurinol (5.4 g), tetraethylammonium chloride (10.8 g), N,N-dimethylaminoaniline (6.2 mL), phosphorous oxychloride (18 mL) and acetonitrile (60 mL) was refluxed for 1.5 hours. The volatile portions were evaporated and the residue stirred with ethyl acetate (500 mL) and ice water (500 mL) for 30 minutes. The organic layer was separated, washed, and dried. Evaporation of the solvent gave a solid which was collected by filtration, washed with cold ethanol and dried to give the product, 4.95 g, mp >250° C.

Example 12

Preparation of 1-O-Methyl-α-L-lyxofuranoside

A solution of L-lyxopyranose (3.0 g, 20 mmol) in 110 mL of methanol and 1.1 mL of 2.5M methanolic hydrochloric acid was stirred for 24 hours and treated with strongly basic resin until pH 7 was obtained. The resin was thoroughly rinsed with methanol and the combined filtrates were concentrated and the residue was chromatographed to obtain 1.62 g of product.

Example 13

Preparation of 1-O-Methyl-2,3,5-tri-O-benzoyl-α-L-lyxofuranoside

A solution of the product of Example 12 (1.5 g), benzoic anhydride (30.8 g) and 1,1-dimethylaminopyridine (10 mg) in 60 mL of pyrimidine was stirred for 18 hours at 40° C. Methanol (25 mL) was added and the mixture concentrated. The residue was dissolved in ethyl acetate, washed with aqueous sodium bicarbonate, dried and solvent removed. The residue was chromatographed to give 4.08 g of product.

Example 14

Preparation of 1-O-Acetyl-2,3,5-tri-O-benzoyl-α-L-lyzofuranoside

To a 0° C. solution of the product of Example 13 (3.5 g) in 3 mL acetic anhydride and 26.6 mL of glacial acetic acid was added 1.6 mL of concentrated sulfuric acid. After 21 hours at room temperature, the mixture was poured over ice, stirred, and extracted with methylene chloride. The organic fractions were combined, washed with aqueous sodium bicarbonate and brine, dried, and the solvent removed. The residue was chromatographed to provide 1.79 g of product.

Examples 15A and 15B

Preparation of 3-Bromo- and 3-(thien-2-yl)-1-(2,3,5-tri-O-benzoyl-1-α-L-lyxofuranosyl)-4-aminopyrazolo[3,4-d]pyrimidine A mixture of the product of Example 14 (2.0 g) and either 3-bromo- (for Example 15A) or 3-(thien-2-yl)-4-aminopyrazolo[3,4-d]pyrimidine (for Example 15B) (2.7 mmol) in 8 mL nitromethane and boron trifluoride etherate (500 μL) was refluxed for 2 hours, cooled in ice and triethylamine (1.1 mL) was added. After 30 minutes, the solvent was removed by coevaporation with ethyl acetate and the residue was chromatographed on silica gel to provide the product.

Examples 16A and 16B

Preparation of 3-Bromo- or 3-(thien-2-yl)-1-(1-α-L-lyxofuranosyl)-4-aminopyrazolo[3,4-d]pyrimidine To a solution of sodium methoxide (0.14M) in methanol was added either the product (0.84 mmol) of Example 15A (for Example 16A) or Example 15B (for Example 16B). After 2 hours, the mixture was adjusted to pH 6 with acidic resin. The mixture was filtered and the resin washed with methanol. The filtrate was concentrated and the residue was chromatographed to give the product; 16A, 50 mg, mp 129°–132° C.; 16B, 70 mg, mp 218°–219° C.

Example 17

Preparation of 4-N-phenylamino-5-phenyl-7-(2,3-O-isopropylidene-1-α-L-lyxofuranosyl)pyrrolo[2,3-d]pyrimidine To a mixture of 4-N-phenylamino-5-bromo-7-(2,3-O-isopropylidene-1-α-L-lyxofuranosyl)pyrrolo[2,3-d]pyrimidine (0.46 g) and Pd(PPh$_3$)$_4$ (116 mg) in diglyme (25 mL) was added PhB(OH)$_2$ (488 mg) dissolved in absolute ethanol and 4 mL of 2M sodium carbonate. The mixture was heated to 100° C. and the reaction monitored by HPLC. After completion of the reaction, the mixture was filtered, concentrated and chromatographed to provide 0.53 g of product.

Example 18

Preparation of 4-N-Phenylamino-5-phenyl-7-(5-O-methanesulfonyl-2,3-O-isopropylidene-1-α-L-lyxofuranosyl)pyrrolo[2,3-d]pyrimidine A solution of lithium diisopropylamide (0.368 mmol) in 1.0 mL THF at −78° C. was added to a solution of 165 mg of the product of Example 17, in 1.5 mL THF at −78° C. After stirring for 5 minutes, MESO$_2$Cl (0.028 mL) in THF was added and the mixture stirred at 10° C. overnight. Aqueous ammonium chloride and ethyl ether was added. The organic layer was separated, dried and concentrated. The residue was chromatographed on silica gel to provide 83 mg of product.

Example 19

Preparation of 4-N-Phenylamino-5-phenyl-7-(2,3-O-isopropylidene-5-deoxy-5-amino-1-α-L-lyxofuranosyl)pyrrolo[2,3-d]pyrimidine A suspension of 83 mg of the product of Example 18 in 12 mL methanol was saturated with ammonia and heated at 80° C. for 3 days in high pressure reaction vessel. The solution was purged with nitrogen, the solvent removed, and the residue chromatographed to provide 56 mg of product.

Example 20

Preparation of 4-N-Phenylamino-5-phenyl-7-(5-deoxy-5-amino-1-α-L-lyxofuranosyl)pyrrolo[2,3-d]pyrimidine A solution of 90 mg of the product of Example 19 in 4.5 mL of 70% trifluoroacetic acid was heated at 60° C. for 40 minutes. The solvent was removed by coevaporation with water (2×5 mL) and ethanol (2×5 mL) and the residue was chromatographed to provide 30 mg of product.

Example 21

2,3-Isopropylidine-1,5-di-O-methyl-L-lyxofuranoside

To a slurry of sodium hydride (2.6 g, 60% in mineral oil) in dimethylformamide (75 mL) was added 1-O-methyl-2,3-isopropylidine-L-lyxofuranoside (7.6 g). After the evolution of gas subsided, iodomethane (4.0 mL) was added and the mixture stirred at 60° C. for 24 hours. Methanol (1 mL) was added and the solvent removed. The residue was dissolved in ethyl acetate, washed twice with water, dried and the solvent removed to provide a colorless oil which was used without further purification, 8.0 g.

Example 22

2,3-Isopropylidine-5-O-methyl-L-lyxofuranose

A solution of product of Example 21 (7.8 g) in aqueous sulfuric acid (0.02M, 200 mL) was heated to 80° C. for 3.5 hours. The mixture was cooled and the pH was adjusted to about 7.5 with 1N aqueous sodium hydroxide. The solvent was removed by coevaporation with DMF (2×20 mL). A solution of the residue in DMF (25 mL), 2,2-dimethoxypropane (10 mL) and p-toluenesulfonic acid (100 mg) was stirred at room temperature for 3 hours. The solvent was removed and the residue chromatographed to obtain the product, 2.5 g.

Example 23

4-Chloro-5-iodo-7-(2,3-isopropylidene-5-O-methyl-1-α-L-lyxofuranosyl)pyrrolo[2,3-d]pyrimidine To a −78° C. solution of product of Example 22 (900 mg) in CCl$_4$ (0.65 mL) and THF (15 mL) was added a solution of hexamethylphosphorous triamide (1.05 mL of 85% solution) in THF (5 mL) over 10 minutes. The mixture was stirred for 1 hour at −78° C., 30 minutes at −15° C. and cooled to −78° C.

To a suspension of sodium hydride (0.3 g, 60% in mineral oil) in CH$_3$CN (25 mL) was added 1.5 g. of 4-chloro-5-iodopyrrolo[2,3-d]pyrimidine. The mixture was stirred for 30 minutes, the cooled chloro sugar prepared above was added and the mixture stirred overnight. Volatile portions were evaporated and the residue chromatographed to give 950 mg of product.

Example 24

4-Chloro-5-iodo-7-(5-O-methyl-1-α-L-lyxofuranosyl)pyrrolo[2,3-d]pyrimidine

A solution of the product of Example 23 (200 mg) in 70% trifluoroacetic acid (10 mL) was stirred at room temperature for 45 minutes. The solvent was removed by coevaporation with water (2×20 mL). Trituration of the residue provided a white solid, 110 mg.

Example 25

4-Amino-5-iodo-7-(5-O-methyl-1-α-L-lyxofuranosyl)pyrrolo[2,3-d]pyrimidine

A solution of the product of Example 24 (100 mg) in methanol (10 mL) saturated with ammonia was heated in a bomb at 110° C. for 12 hours. The bomb was cooled and the excess ammonia was allowed to evaporate. Removal of the solvent provided a residue which was crystallized from ethanol (30 mL) to give the product, 75 mg, mp 218°–219° C.

Example 26

5-Iodo-4-N-phenylamino-7-(2,3-isopropylidene-5-O-methyl-1-α-L-lyxofuranosyl)pyrrolo[2,3-d]pyrimidine A mixture of the product of Example 23 (180 mg), aniline (0.2 mL) and ethanol (10 mL) was refluxed for 24 hours. The solvent was removed and the residue was chromatographed to obtain the product, 350 mg.

Example 27

5-Phenyl-4-phenylamino-7-(5-O-methyl-1-α-L-lyxofuranosyl)pyrrolo[2,3-d]pyrimidine A solution of the product of Example 26 (350 mg), phenylboronic acid (230 mg), palladium tetrakis-triphenylphosphine, diglyme (10 mL) and aqueous sodium carbonate (1 mL, 1N) was heated to 100° C. for 4 hours. The solvent was evaporated and the residue was stirred with 70% trifluoroacetic acid (10 mL) for 45 minutes. Volatile portions were evaporated and the residue was chromatographed to obtain the product, 100 mg, mp 162°–163° C.

Example 28

5-Deoxy-1-O-methyl-2,3-isopropylidene-L-lyxofuranoside

A solution of 5-deoxy-2,3-isopropylidene-β-D-erythropent-4-enofuranoside (8 g) in 150 mL of methanol was hydrogenated in the presence of a catalytic amount of palladium on carbon for 24 hours. The mixture was filtered and the solvent removed to give the product, 8 g.

Example 29 b 5-Deoxy-2,3-isopropylidene-L-lyxofuranoside

A mixture of the compound from example 29 (7.0 g) in 5 mL of concentrated sulfuric acid and 500 mL of water was heated at 85° C. for 3 hours. The pH of the solution was adjusted to approximately 7 with 1N aqueous NaOH. The solvent was evaporated and the residue coevaporated with DMF. The residue was dissolved in DMF (60 mL). To the filtered mixture was added 10 mL of 2,2-dimethoxypropane and 100 mg of p-toluenesulfonic acid and the mixture stirred for 3 hours. The solvent was removed and the residue chromatographed to give the product, 5.0 g.

Example 30

4-Chloro-5-iodo-7-(5-deoxy-2,3-isopropylidene-1-α-L-lyxofuranosyl)pyrrolo[2,3-d]pyrimidine The title compound was synthesized following a procedure analogous to the synthesis as described in Example 23, starting from 2.3 g of the sugar prepared in Example 29 and 2.8 g of 4-chloro-5-iodopyrrolo[2,3-d]pyrimidine to give the product, 0.97 g.

Example 31

4-Amino-5-iodo-7-(5-deoxy-1-α-L-lyxofuranosyl)pyrrolo[2,3-d]pyrimidine

The product from Example 30 (200 mg) was heated with methanolic ammonia in a bomb at 110° C. for 20 hours. After normal work up, the residue was treated with 70% trifluoroacetic acid and recrystallized from ethanol to give the product, 100 mg, mp 225°–226° C.

Example 32

5-Iodo-4-(phenylamino)-7-(5-deoxy-1-α-L-lyxofuranosyl)pyrrolo[ 2,3-d]pyrimidine

A mixture of the product from Example 30 (200 mg), aniline (150 mg) and ethanol was refluxed for 8 hours. The solvent was evaporated and the residue chromatographed. The product thus obtained was treated with 70% trifluoroacetic acid and worked up in the usual manner to give the product, 200 mg, mp 219°–221° C.

Example 33

4-(Phenylamino)-5-phenyl-7-(5-deoxy-1-α-L-lyxofuranosyl)pyrrolo[ 2,3-d]pyrimidine The title compound was synthesized following a procedure analogous to the synthesis as described in Example 27, starting from 180 mg of the product prepared in Example 32 and 2.8 g of 4-chloro-5-iodopyrrolo[2,3-d]pyrimidine to give the product, 100 mg, mp 224°–225° C.

Example 34

5-Bromo-4-chloro-7-(5-deoxy-2,3-isopropylidene-1-α-L-lyxofuranosyl)pyrrolo[2,3-d]pyrimidine The title compound was synthesized following a procedure analogous to the synthesis as described in Example 30, by condensation of 5-bromo-4-chloropyrrolo[2,3-d] pyrimidine (2.6 g) with the chloro sugar to give the product, 0.92 g.

Example 35

4-Amino-5-bromo-7-(5-deoxy-1-α-L-lyxofuranosyl)pyrrolo[2,3-d]pyrimidine

The product from Example 34 was heated with methanolic ammonia at 110° C. in a bomb and the compound obtained after normal work up was treated with 70% trifluoroacetic acid at 40° C. for 30 minutes. The trifluoroacetic acid was evaporated and the residue was coevaporated with water (2×10 mL) and recrystallized from ethanol to give the product, 50 mg, mp 231°–233° C.

Example 36

4-(Phenylamino)-5-phenyl-7-(2,3,5-tri-O-acetyl-1-α-L-lyxofuranosyl)pyrrolo[ 2,3-d]pyrimidine The compound from Example 17 (100 mg) was stirred with pyridine (5 ml) and acetic anhydride (1.5 mL) at room temperature. The volatile portions were evaporated and the residue chromatographed to give the product as a foam.

Example 37

Preparation of 4-(Phenylamino)-3-phenylpyrazolo[ 3,4-d]pyrimidine

A mixture of the compound from example 37 (4.8 g), aniline (6 mL) and ethanol was heated in a bomb at 100° C. for 12 hours. The usual workup (described in Example 35) and recrystallization from ethanol gave the product, 4.0 g.

Example 38

Preparation of 4-(Phenylamino)-3-phenyl-1-(2,3,5-tri-O-benzoyl-1-α-L-lyxofuranosyl)pyrazolo[3,4-d]pyrimidine Following a procedure similar to that of Examples 15A and 15B, the products from Examples 14 and 38 were coupled on a 3.5 mmol scale to obtain the product as a foam, 680 mg.

Example 39

Preparation of 4-(Phenylamino)-1-(1-α-L-lyxofuranosyl)pyrazolo[ 3,4-d]pyrimidine The product of example 39 (670 mg) was dissolved in methanol (20 mL) and treated with sodium methoxide. The mixture was stirred for 1 hour and the pH was adjusted to 3.5 with acidic resin. The mixture was filtered and the filtrate was evaporated. Chromatography of the residue gave the product, 300 mg, mp 234°–235° C.

For convenience, adenosine kinase inhibitor compounds in the following examples are referred to by numbers. The following is a listing of chemical names and compound numbers: 4-amino-5-iodo-7-(1-alpha-L-lyxofuranosyl)pyrrolo[ 2,3-d]pyrimidine (compound A), 4-(phenylamino)-5-phenyl- 7-(1-alpha-L-lyxofuranosyl)pyrrolo[2,3-d]pyrimidine (compound B) AND 4-amino-5-iodo-7-(5-amino-5-deoxy-1-alpha-L-lxyofuranosyl)-pyrrolo[ 2,3-d]pyrimidine (compound C), 4-N-phenylamino- 5-phenyl-7-(5-deoxy-1-alpha-L-lyxofuransoyl)pyrrolopyrimidine (compound D), and 1-(1-alpha-L-lyxofuranosyl)- 3-phenyl-4-phenylaminopyrazolo[3,4-d]pyrimidine (compound E).

Example A

Inhibition of Adenosine Kinase Activity

Inhibition of enzyme activity was determined using a 0.1 ml assay mixture containing 50 mM Tris-maleate, pH 7.0, 0.1% (w/v) BSA, 1 mM ATP, 1 mM $MgCl_2$, 0.5 µM [U-$^{14}$C] adenosine (500 mCi/mmol) and 0.1 µg of purified pig heart adenosine kinase. Different concentrations of the test compounds were incubated in the assay mixture for 20 minUTES at 37° C. From each reaction mixture, 20 µl portions were removed and spotted on 2 $cm^2$ pieces of Whatman DE 81 filter paper. The papers were then washed to remove [$^{14}$C] adenosine in 1 mM ammonium formate followed by deionized water and finally 95% ethanol. The papers were dried, and [$^{14}$C]AMP measured by scintillation counting. Activities were determined from the amount of [$^{14}$C]AMP formed.

$A_1$ receptor binding affinity was determined using 0.5 ml mixture containing 50 mM Tris HCl, pH 7.4, 1 nM [$^3$H]CHA and 0.5 mg of neuronal membrane incubated with different concentrations of the test compound for 60 minutes at 37° C. The reaction was stopped and unbound [$^3$H]CHA removed by rapid filtration through Whatman GF/B filters. The filter papers were then solubilized and bound [$^3$H]CHA determined by scintillation counting.

Inhibition of adenosine deaminase activity was determined spectrophotometrically using a 1 ml assay mixture containing 50 mM potassium phosphate, pH 7.0, 1 mM ADP, 2.5 mM alpha-ketoglutarate, 15 units glutamic dehydrogenase, 0.125 mM NADH, 80 µM adenosine and 0.002 units of calf intestinal mucosa adenosine deaminase. Different concentrations of the test compounds were incubated in the assay mixture for 10 min at 37° C. The reaction was monitored continuously for oxidation of NADH from the change in absorbance at 340 nm.

Illustrative of the invention, the following compounds were showed to be highly potent inhibitors of adenosine kinase activity. Compound A was found to have an $IC_{50}$ value of 68 nM. Compound B was found to have an $IC_{50}$ value of 0.46 nM while compound C was found to have an $IC_{50}$ value of 36 nM. Thus the amount of compound of the present invention necessary to inhibit the adenosine kinase is quite small. In contrast, the ability to inhibit this enzyme with the known compound, 9-(α-L-lyxofuranosyl)adenine, was measured using these conditions. The $IC_{50}$ of this compound was found to be greater than 10,000 nM. Therefore compound B of the present invention is more than twenty thousand times more potent an inhibitor of adenosine kinase than 9-(α-L-lyxofuranosyl)-adenine.

Example B

Adenosine Kinase Inhibition in Intact Cells

Inhibition of adenosine kinase in intact cells was determined from the amount of incorporation of radioisotope from adenosine into the adenylates (AMP, ADP and ATP) in the presence of adenosine deaminase inhibition. Capillary endothelial cells from bovine heart were incubated for 60 minutes with 20 μM 2'-deoxycoformycin, a potent adenosine deaminase inhibitor. Different concentrations of the test compounds were then added to the cells and incubated for 15 minUTES after which 5 μM [$^3$H]adenosine was added and the cells incubated for a further 15 minutes. The media was then discarded and the cells were treated with 50 μl 0.4M perchloric acid, centrifuged and the supernatants neutralized with 100 μl alanine: freon (1:4). Radioisotope labelled adenylates were separated by TLC on PEI cellulose plates developed in methanol:water (1:1) and incorporation of $^3$H determined by scintillation counting.

Illustrative of the invention, compound A, compound B, compound C, compound D and compound E were shown to possess $IC_{50}$ values in the adenosine kinase inhibition assay in intact cells of 7.3 μM, 1.1 μM, 100 μM and 0.0028 μM respectively.

Example C

Adenosine Kinase Inhibition in Whole Animals

Inhibition of adenosine kinase in whole animals was determined using 5-amino-1-β-D-ribofuranosyl-imidazole (acadesine; AICAr) and taking advantage of the fact that adenosine kinase catalyzes the phosphorylation of acadesine to 5-amino-1-β-D-ribofuranosyl-imidazole-4-carboxamide monophosphate (ZMP). Administration of acadesine leads to readily detectable levels of ZMP in the tissues or organs of interest within the animal. A mouse model has been used to provide data on the potency of test compounds together with information on their biological half life, oral bioavailability and brain penetration.

Test compounds were administered intravenously by tail vein injection at 1 mg/kg or orally at 10 mg/kg followed 30 minutes, 150 minutes or 450 minutes later by intraperitoneal administration of acadesine at a dose of 500 mg/kg. After 30 minutes the organs of interest (e.g., heart, brain) were removed, freeze clamped, homogenized and the tissue extracted and its contents were analyzed for acadesine and ZMP by HPLC.

Figure 2:
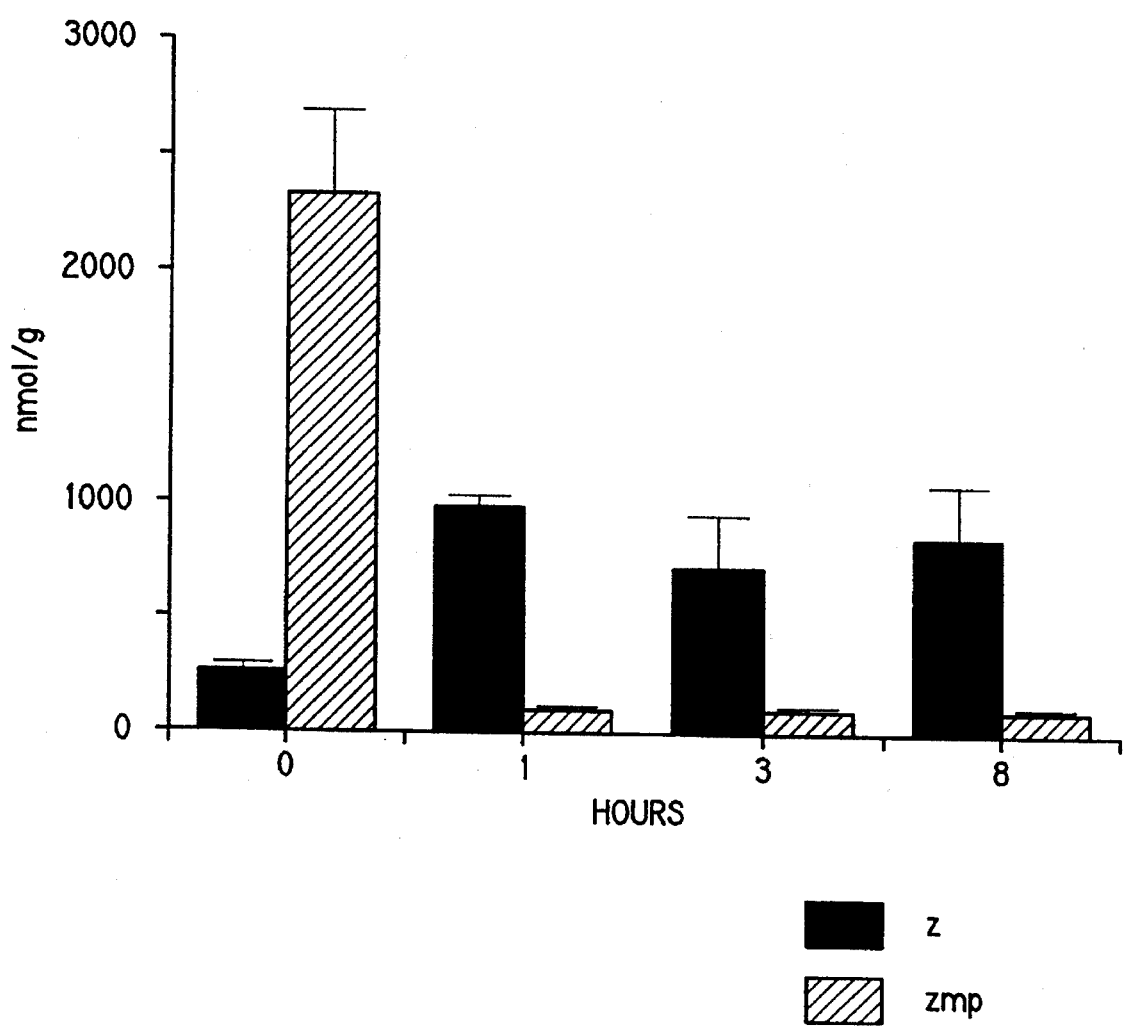
FIG. 2 depicts acadesine and ZMP levels in heart tissue after oral administration of one of the compounds of the present invention as described Example C.

FIGS. 1 and 2 depict levels of acadesine and ZMP in heart tissue after IV (FIG. 1) and oral (FIG. 2) administration of the compound of the present invention 4-amino-5-iodo-7-(1-alpha-L-lyxofuranosyl)pyrrolo[2,3-d]pyrimidine (Compound A).

Using the same technique, the ability of orally administered (10 mg/kg) compound D to inhibit adenosine kinase in the rat was measured. Compound D was found to completely inhibit adenosine kinase for a period of three hours and to partially inhibit adensoinse kinse for a period of eight hours.

Example D

Improved Functional Recovery in Ischemic Hearts

The ability of a number of adenosine kinase inhibitors to improve the recovery of post-ischemic function was examined in an isolated guinea pig heart model.

Isolated guinea pig hearts were cannulated via the ascending aorta and attached to a perfusion apparatus according to the method of Langendorff. The hearts were perfused at a constant pressure of 60 cm of water with a modified Krebs-Hanseleit buffer (pH 7.4) at 37° C. Left ventricular developed pressures (LVDP) were monitored continuously using a latex balloon attached to a pressure transducer. Coronary flows were measured gravimetrically by timed collection of pulmonary effluent. Following equilibration of the hearts for a period of 30 minutes, the hearts were subjected to 45 minutes of low flow ischemia, by reducing the perfusion pressure to 10 cm of water, and then roperfused for 30 minutes by restoring the pressure to its original level (60 cm of water). The adenosine kinase inhibitor, 4-amino-5-iodo-7-(1-alpha-L-lyxofuranosyl)pyrrolo[2,3-d]pyrimidine (compound A), 4-(phenylamino)-5-phenyl- 7-(1-alpha-L-lyxofuranosyl)pyrrolo[2,3-d]pyrimidine (compound B) or 4-amino-5-iodo-7-(5-amino-5-deoxy-1-alpha-L-lxyofuranosyl)pyrrolo[ 2,3-d]pyrimidine (compound C), was added to the perfusion buffer at the specified concentrations. The results of these experiments are shown in Table I and demonstrate that adenosine kinase inhibitors enhance recovery of post ischemic function.

Figure 3:
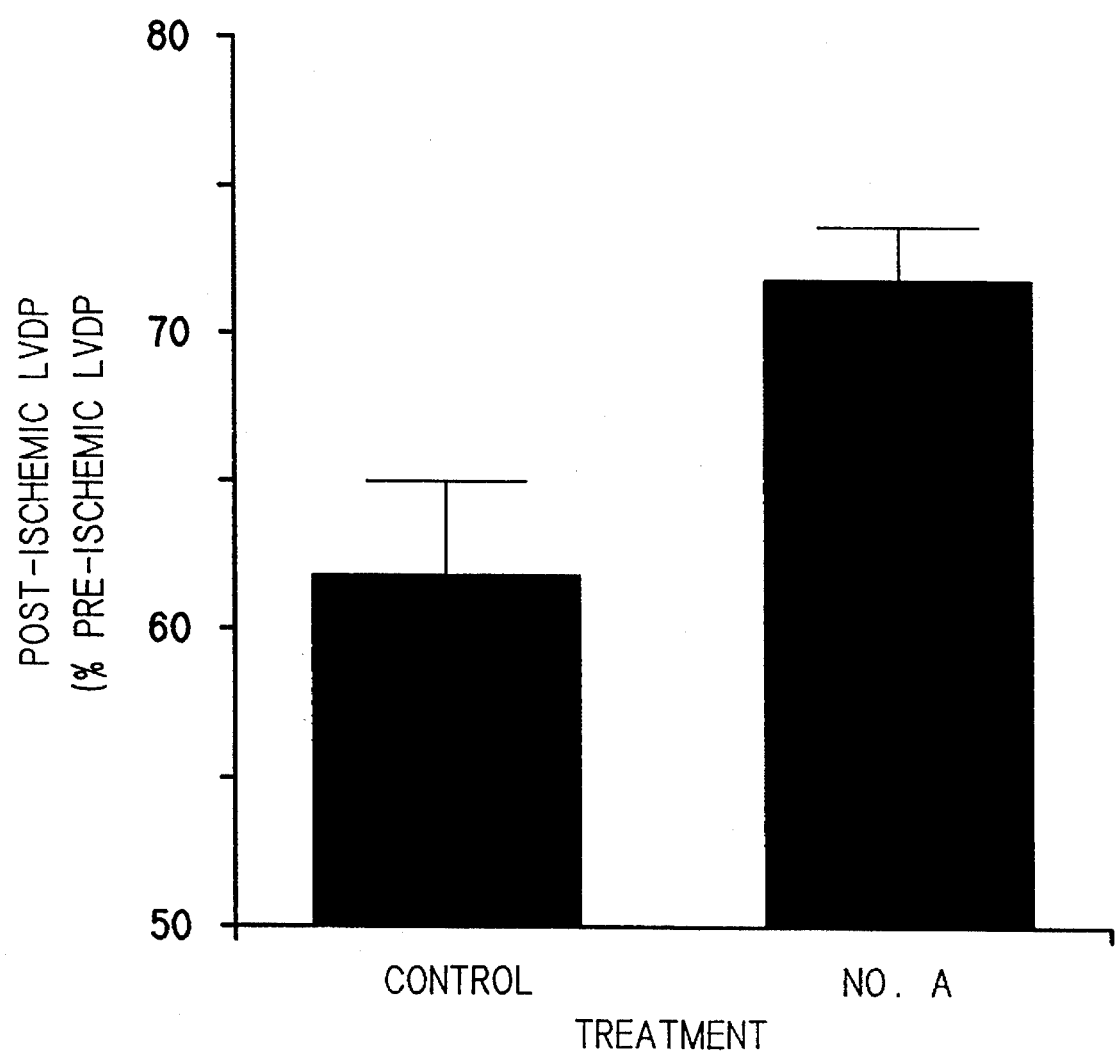
FIG. 3 depicts improved recovery of post-ischemic function by one of the compounds of the present invention as described in Example D.

FIG. 3 depicts improved recovery of post-ischemic function by 4-amino-5-iodo-7-(1-alpha-L-lyxofuranosyl)pyrrolo[ 2,3-d]pyrimidine (Compound A).

TABLE I

Effect of Test Compound on Recovery of Post-Ischemic Function in the Isolated Guinea Pig Heart

| Inhibitor | Conc (μM) | LVDP (% of Pre-I LVDP) |
|---|---|---|
| Control | — | 62.1 ± 2.7 |
| Compound A | 1 | 71.4 ± 1.5* |
| Control | — | 62.5 ± 3.7 |
| Compound C | 1 | 66.3 ± 3.0 |
|  | 10 | 72.3 ± 2.8+ |

*p < 0.05 vs. Control
+ p < 0.1 vs. Control

Example E

An AK Inhibitor is Beneficial in a Model of Chronic Arthritis

Male Lewis rats (150–200 g) were immunized at the base of the tail with 1 mg of heat-killed mycobacteria butyricum in 100 μl of mineral oil. Initial paw volumes were measured by plethysmometry. Beginning on day 8 after immunization, daily paw volumes were measured and animals were gavaged with vehicle, compound B 5 mg/kg qd or compound B 5 mg/kg bid. On day 10, animals developed a progressive inflammatory arthritis with histopathologic and clinical features similar to those observed in rheumatoid arthritis. On day 21, the experiment was terminated. Heparinized blood was drawn for hematologic studies and radiographs were obtained of the hind paws to study bone destruction. FIG. 3 shows that compound B significantly decreased paw swelling in adjuvant arthritis. The table below lists hematologic parameters (Hematocrit is expressed as a percentage and white blood cells are $10^3$ cells/mm$^3$.) from this experiment and show that leukopenia (as is often observed with immunosuppressive agents) was not observed. One major problem with current treatments for rheumatoid arthritis is the dissociation between symptomatic improvement and continued progression of bone and cartilage damage. Surprisingly, compound B decreased joint destruction in adjuvant arthritis as judged by standard radiographic criteria (see Table II below.)

TABLE II

Effect of Compound B on radiographic and hematologic parameters in adjuvant arthritis

| | Radiographic Score* | Hematocrit | WBC |
| --- | --- | --- | --- |
| Control | 2.78 ± 0.15 | 38.4 ± 0.8 | 9.8 ± 1.4 |
| Compound B (5 mg/kg q.d.) | 1.43 ± 0.43** | 37.1 ± 0.5 | 10.6 ± 0.8 |
| Compound B (5 mg/kg b.i.d) | 1.67 ± 0.33** | 45.3 ± 7.3 | 8.4 ± 1.2 |

*0 = normal;
1+ = soft tissue swelling;
2+ = mild periosteal reaction;
3+ = destruction of cortical bone and/or ankylosis
**p < 0.01 compared to control

We claim
1. A compound of the formula

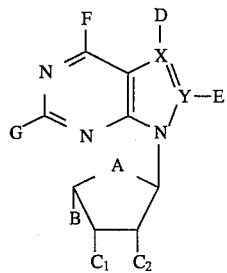

wherein

A is oxygen, methylene or sulfur;

B is carboxyl, carboxyalkyl, carboxamido, alkenyl, or —(CH$_2$)$_n$—B' wherein n is an integer from 1 to 5 and B' is hydrogen, hydroxy, lower alkyl esters or carbonate esters thereof, alkyl, alkoxy, amino, alkylamino, mercapto, alkylthio, halogen, azido, cyano, aminocarboxyalkyl, or amidoalkyl;

C$_1$ and C$_2$ are independently hydrogen, hydroxyl or lower alkyl esters or carbonate esters thereof, or when taken together form a lower cyclic ring containing two or more oxygen atoms;

X and Y are independently carbon or nitrogen, however both X and Y cannot be nitrogen;

D is halogen, alkyl, aryl, aralkyl, alkenyl, alkynyl, alkoxy, cyano, cyanoalkyl, carboxamido, aryloxy, amino, alkylamino, arylamino, aralkylamino, alkylthio, or arylthio when X is carbon, and is null when X is nitrogen;

E is hydrogen, halogen, alkyl, alkylamino, alkylthio or azido when Y is carbon and is null when Y is nitrogen;

F is amino, hydrogen, halogen, alkoxy, alkylthio, aryl, alkyl, alkylamino, arylamino, or aralkylamino;

G is hydrogen, lower alkyl, halogen, alkoxy or alkylthio;

and pharmaceutically acceptable salts thereof;

with the proviso that when X is nitrogen and Y is carbon, E and G are hydrogen and F is amino, then B is not methyl, hydroxymethyl or vinyl.

2. A compound of claim 1 wherein A is oxygen.

3. A compound of claim 1 wherein B is —(CH$_2$)$_n$—B' and n is 1.

4. A compound of claim 1 wherein B is —(CH$_2$)$_n$—B' and B' is hydrogen, amino, hydroxy, or lower alkoxy.

5. A compound of claim 1 wherein C$_1$ and C$_2$ are independently hydroxy or hydrogen or wherein C$_1$ and C$_2$ taken together form a lower cyclic ring containing two or more oxygen atoms.

6. A compound of claim 1 wherein C$_1$ and C$_2$ are independently lower alkyl esters.

7. A compound of claim 1 wherein X and Y are carbon.

8. A compound of claim 1 wherein X is carbon and Y is nitrogen.

9. A compound of claim 1 wherein G is hydrogen.

10. A compound of claim 1 wherein D is halogen.

11. A compound of claim 1 wherein D is optionally substituted aryl or heteroaryl.

12. A compound of claim 1 wherein E is hydrogen.

13. A compound of claim 1 wherein F is amino, alkylamino, or optionally substituted arylamino.

14. A compound of claim 1 wherein A is oxygen, B is —(CH$_2$)$_n$—B', n is 1–5, X and Y are carbon.

15. A compound of claim 14 wherein n is 1, C$_1$ and C$_2$ are hydroxy and B' is hydrogen, hydroxy, amino, alkoxy or alkyl.

16. A compound of claim 15 wherein E and G are hydrogen.

17. A compound of claim 16 wherein D is halogen.

18. A compound of claim 17 wherein F is amino, alkylamino or arylamino.

19. A compound of claim 17 wherein F is anilino or substituted anilino.

20. A compound of claim 16 wherein D is phenyl or substituted phenyl.

21. A compound of claim 20 wherein F is amino, alkylamino or arylamino.

22. A compound of claim 20 wherein F is anilino or substituted anilino.

23. A compound of claim 1 wherein A is oxygen, B is —(CH$_2$)$_n$—B', n is 1–5, X is carbon and Y is nitrogen.

24. A compound of claim 23 wherein n is 1, C$_1$ and C$_2$ are hydroxy and B' is hydrogen, hydroxy, amino, alkoxy or alkyl.

25. A compound of claim 24 wherein E is null and G is hydrogen.

26. A compound of claim 25 wherein D is halogen.

27. A compound of claim 26 wherein F is amino, alkylamino or arylamino.

28. A compound of claim 26 wherein F is anilino or substituted anilino.

29. A compound of claim 25 wherein D is aryl.

30. A compound of claim 29 wherein F is amino, alkylamino or arylamino.

31. A compound of claim 29 wherein F is anilino or substituted anilino.

32. A compound of claim 1 wherein A is oxygen, B is —CH$_3$, C$_1$ and C$_2$ are hydroxy, E and G are hydrogen, X and Y are carbon, D is iodine and F is amino.

33. A compound of claim 1 wherein A is oxygen, B is —CH$_2$—OH, C$_1$ and C$_2$ are hydroxy, E and G are hydrogen, X and Y are carbon, D is iodine and F is chlorine.

34. A compound of claim 1 wherein A is oxygen, B is —CH$_2$—OH, C$_1$ and C$_2$ are hydroxy, E and G are hydrogen, X and Y are carbon, D is iodine and F is amino.

35. A compound of claim 1 wherein A is oxygen, B is —CH$_2$—OH, C$_1$ and C$_2$ are hydroxy, E and G are hydrogen, X and Y are carbon, D is bromine and F is chlorine.

36. A compound of claim 1 wherein A is oxygen, B is —CH$_2$—OH, C$_1$ and C$_2$ are hydroxy, E and G are hydrogen, X and Y are carbon, D is phenyl and F is anilino.

37. A compound of claim 1 wherein A is oxygen, B is —CH$_2$—NH$_2$, C$_1$ and C$_2$ are hydroxy, E and G are hydrogen, X and Y are carbon, D is phenyl and F is anilino.

38. A compound of claim 1 wherein A is oxygen, B is —CH$_2$—NH$_2$, C$_1$ and C$_2$ are hydroxy, E and G are hydrogen, X and Y are carbon, D is iodine and F is amino.

39. A compound of claim 1 wherein A is oxygen, B is —CH$_3$, n is 1–5, C$_1$ and C$_2$ are hydroxy, E and G are hydrogen, X and Y are carbon, D is iodine and F is anilino.

40. A compound of claim 1 wherein A is oxygen, B is —CH$_2$—OH, C$_1$ and C$_2$ are hydroxy, E and G are hydrogen, X and Y are carbon, D is iodine and F is anilino.

41. A compound of claim 1 wherein A is oxygen, B is —(CH$_2$)$_n$—B', n is 1, B', C$_1$ and C$_2$ are acetoxy, E and G are hydrogen, X and Y are carbon, D is phenyl and F is anilino.

42. A compound of claim 1 wherein A is oxygen, B is —CH$_2$OCH$_3$, C$_1$ and C$_2$ are hydroxy, E and G are hydrogen, X and Y are carbon, D is phenyl and F is anilino.

43. A compound of claim 1 wherein A is oxygen, B is —CH$_2$—OH, C$_1$ and C$_2$ are hydroxy, E is null, G is hydrogen, X is carbon and Y is nitrogen, D is phenyl and F is anilino.

44. A compound of claim 1 wherein A is oxygen, B is —CH$_3$, E and G are hydrogen, C$_1$ and C$_2$ are hydroxy, X and Y are carbon, D is phenyl and F is anilino.

45. A compound of claim 1 wherein A is oxygen, B is —CH$_2$OH, C$_1$ and C$_2$ are hydroxy, E and G are hydrogen, X and Y are carbon, D is bromo and F is amino.

46. A compound of claim 1 wherein A is oxygen, B is —CH$_3$, C$_1$ and C$_2$ are hydroxy, E and G are hydrogen, X and Y are carbon, D is iodo and F is chloro.

47. A compound of claim 1 wherein A is oxygen, B is —CH$_2$NH$_2$, C$_1$ and C$_2$ are hydroxy, E is null, G is hydrogen, X is carbon and Y is nitrogen, D is bromo and F is amino.

48. A compound of claim 1 wherein A is oxygen, B is —CH$_2$NH$_2$, C$_1$ and C$_2$ are hydroxy, E is null, G is hydrogen, X is carbon and Y is nitrogen, D is phenyl and F is phenylamino.

49. A compound of claim 1 wherein A is oxygen, B is —CH$_2$OH, C$_1$ and C$_2$ are hydroxy, E and G are hydrogen, X and Y are carbon, D is phenyl and F is 4-fluorophenylamino.

50. A compound of claim 1 wherein A is oxygen, B is —CH$_2$OH, C$_1$ and C$_2$ are hydroxy, E and G are hydrogen, X and Y are carbon, D is iodo and F is 2-pyridylmethylamino.

51. A compound of claim 1 wherein A is oxygen, B is —CH$_2$OH, C$_1$ and C$_2$ are hydroxy, E and G are hydrogen, X and Y are carbon, D is phenyl and F is (4-ethoxyphenyl)amino.

* * * * *

UNITED STATES PATENT AND TRADEMARK OFFICE
CERTIFICATE OF CORRECTION

PATENT NO. : 5,506,347
DATED : April 9, 1996
INVENTOR(S) : Mark D. Erion, et al.

It is certified that error appears in the above-identified patent and that said Letters Patent is hereby corrected as shown below:

Column 1, Line 7: delete "08/192,391" and insert --08/182,381--

Column 1, Line 9: delete "09/014,159" and insert --08/014,159--

Column 13, Line 58: delete "rosylate" and insert --tosylate--

Column 15, Line 56: delete "z" and insert --2--

Column 26, Line 49: delete "presnt" and insert --present--

Column 38, Line 44: delete "minUTES" and insert --minutes--

Column 39, Line 31: delete "minUTES" and insert --minutes--

Column 40, Line 10: delete "kinse" and insert --kinase--

UNITED STATES PATENT AND TRADEMARK OFFICE
CERTIFICATE OF CORRECTION

PATENT NO. : 5,506,347
DATED : April 9, 1996
INVENTOR(S) : Mark D. Erion, et al.

It is certified that error appears in the above-identified patent and that said Letters Patent is hereby corrected as shown below:

Column 40, Line 30: delete "roperfused" and insert --reperfused--

Signed and Sealed this

Twenty-fifth Day of November, 1997

Attest:

Attesting Officer

BRUCE LEHMAN

Commissioner of Patents and Trademarks